(12) United States Patent
Alnemri

(10) Patent No.: US 6,207,801 B1
(45) Date of Patent: Mar. 27, 2001

(54) FADD-LIKE ANTI-APOPTOTIC MOLECULES, METHODS OF USING THE SAME, AND COMPOSITIONS FOR AND METHODS OF MAKING THE SAME

(75) Inventor: Emad S. Alnemri, Ambler, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/276,993

(22) Filed: Mar. 26, 1999

Related U.S. Application Data

(62) Division of application No. 08/859,167, filed on May 20, 1997, now Pat. No. 6,037,461.
(51) Int. Cl.$^7$ .......................... C07K 14/47; C12P 21/06; C12N 15/00; G01N 33/574; A61K 38/17
(52) U.S. Cl. .................. 530/350; 536/23.5; 435/69.1; 435/320.1; 435/7.23; 435/7.1; 530/324; 514/44; 424/185.1
(58) Field of Search .................. 536/23.5; 435/69.1, 435/320.1, 7.23, 7.1; 530/324, 350; 514/44; 424/185.1

(56) References Cited

U.S. PATENT DOCUMENTS

| | | |
|---|---|---|
| 4,736,866 | 4/1988 | Leder et al. |
| 4,873,191 | 10/1989 | Wagner et al. |
| 5,108,921 | 4/1992 | Denny et al. |

OTHER PUBLICATIONS

Ahmad, et al., "CRADD, a Novel Human Apoptotic Adaptor Molecule for Caspase–2, and FasL/Tumor Necrosis Factor Receptor–interacting Protein RIP$^1$", Cancer Res., 1997, 57, 615–619.

Alnemri, et al, "Human ICE/CED–3 Protease Nomenclature", Cell, 1996, 87, 171.

Alnemri, "Mammalian Cell Death Proteases: A Family of Highly Conserved Aspartate Specific Cysteine Proteases", J. Cell. Biol., 1997, 64, 33–42.

Arad, et al., "Use of reconstituted Sendai virus envelopes for fusion–mediated microinjection of double–stranded RNA: inhibition of protein synthesis in interferon–treated cells", Biochim, Biophys. Acta, 1986, 859, 88–94.

Bertin, et al., "Apoptotic Suppression by Baculovirus P35 Involves Cleavage by and Inhibition of a Virus–Induced CED–3/ICE–Like Protease", J. Virol., 1996, 70, 6251–6259.

Boldin, et al., "Involvement of MACH, a Novel MORT1/FADD–Interacting Protease, in Fas/APO–1– and TNF Receptor–Induced Cell Death", Cell, 1996, 85, 803–815.

Brown, "Gene therapy oversold by researchers, journalists", Washington Post, Dec. 8, 1996, A1 and A22.

Bullrich, et al., "Chromosomal Mapping of Members of the cdc2 Family of Protein Kinases, cdk3, cdk6, PISSLRE, and PITALRE, and A cdk Inhibitor, p27$^{Kip1}$, to Regions Involved in Human Cancer", Cancer Research, 1995, 55, 1199–1205.

Capecchi, M.R., "Altering the Genome by Homologous Recombination", Science, 1989, 244, 1288–1292.

Dermer, "Another anniversary for the was on cancer", Bio/Tech ., 1994, 12, 320.

Fernandes–Alnemri, et al., "In vitro activation of CPP32 and Mch3 by Mch4, a novel human apoptotic cysteine protease containing two FADD–like domains", Proc. Natl. Acad. Sci. USA, 1996, 93, 7464–7469.

Fernandes–Alnemri, et al., "CPP32, a Novel Human Apoptotic Protein with Homology to Caenorhabditis elegans Cell Death Protein Ced–3 and Mammalian Interleukin–1 β–converting Enzyme", J. Biol. Chem., 1994, 269, 30761–30764.

Gura, "Systems for identifying new drugs are often faulty", Science, 1997, 278, 1041–1042.

Henkart, P.A., "ICE Family Proteases: Mediator of All Apoptotic Cell Death", Immunity, 1996, 4, 195–201.

Li, et al., "Mice Deficient in IL–1β–Converting Enzyme Are Defective in Production of Mature IL–1β and Resistent to Endotoxic Shock", Cell, 1995, 80, 401–411.

Lu, et al., "UV irradiation–induced apoptosis leads to activation of a 36–kDa myelin basic protein kinase in HL–60 cells", Proc. Natl. Acad. Sci. USA, 1996, 93, 8977–8982.

Muzio, et al., "Flice, A Novel FADD–Homologous ICE/CED–3–like Protease, Is Recruited to the CD95 (Fas/APO–1) Death–Inducing Signaling Complex", Cell, 1996, 85, 817–827.

Nagata, S., "Apoptosis by Death Factor", Cell, 1997, 88, 355–365.

Nagata, S., "Fas–Mediated Apoptosis", Adv. Exp. Med. Biol., 1996, 406, 119–124.

Nagata, S. And Golstein, P., "The Fas Death Factor", Science, 1995, 267, 1449–1456.

Nagata, S., "Fas and Fas Ligand: A Death Factor and Its Receptor", Adv. Immunol., 1994, 57, 129–144.

(List continued on next page.)

Primary Examiner—Phuong T. Bui
(74) Attorney, Agent, or Firm—Woodcock Washburn Kurtz Mackiewicz & Norris LLP

(57) ABSTRACT

Two FADD-like anti-apoptotic proteins that regulate Fas/TNFR1- or UV-induced apoptosis are disclosed. Nucleotide sequences encoding the proteins are disclosed as are methods of using the nucleic acid molecules and making the proteins. Pharmaceutical compositions and methods of using the same are disclosed. Reagents, kits and methods of identifying compounds that inhibit anti-apoptotic activity of the proteins and methods of identifying compounds that inhibit binding activity of the proteins are disclosed.

3 Claims, 12 Drawing Sheets

OTHER PUBLICATIONS

Orkin, "Report and recommendations of the panel to assess the NIH investment in research on gene therapy", Dec. 7, 1995, 41 pages.

Rosette, C. and Karin, M., "Ultraviolet Light and Osmotic Stress: Activation of the JNK Cascade Through Multiple Growth Factor and Cytokine Receptors", *Science*, 1996, 274, 1194–1197.

Srinivasula et al., "FLAME–1, a novel FADD–like anti–apoptotic molecule that regulates Fas/TNFR1–induced apoptosis", *J. Biol. Chem.*, 1997, 272(30), 18542–18545.

Srinivasula, et al., "Molecular ordering of the Fas–apoptotic pathway: The Fas/APO–1 protease Mch5 is a CrmA–inhibitable protease that activates multiple Ced–3/ICE–like cysteine proteases", *Proc. Natl. Acad. Sci. USA,* 1996, 93, 14486–14491.

Ullrich, et al., "Insulin–like growth factor I receptor primary structure: comparison with insulin receptor suggests structural determinants that define functional specificty", *EMBO J.,* 1986, 5, 2503–2512.

Ware, et al., "Apoptosis Mediated by the TNF–Related Cytokine and Receptor Families", *J. Cell. Biochem.,* 1996, 60, 47–55.

FIGURE 1A

```
FLAME-1    1   ................MSAEVIHQVEEALDTDEKEMLLFLCRDVAIDV
Mch5-beta  1   ................MDFSRNLYDIGEQLDSEDLASLKFLSLDYIPQR
Mch4       1   MKSQGQHWYSSSDKNCKVSFREKLLIIDSNLGVQDVENLKFLCIGLVPNK FLAME-1    33  VPPNVRD...LLDILRERGKLSVGD...LAELLYRVRRFDLLKRILKMDR
Mch5-beta  34  KQEPIKDALMLFQRLQEKRMLEESNLSFLKELLFRINRLDLLITYLNTRK
Mch4       51  KLEKSSSASDVFEHLLAEDLLSEEDPFFLAELLY.IIRQKKLLQHLNCTK FLAME-1    77  KAVETHL.LRNPHLVSDYRVLMAEIGEDLDKSDVSSLIFLMKDYMGRGKI
Mch5-beta  84  EEMERELQTPGRAQISAYRVMLYQISEEVSRSELRSFKFLLQEEISKCKL
Mch4       100 EEVERLL..PTRQRVSLFRNLLYELSEGIDSENLKDMIFLLKDSLPK...

FLAME-1    126 SKEKSFLDLVVELEKLNLVAPDQLDLLEKCLKNIHRIDLKTKIQKYKQSV
Mch5-beta  134 DDDMNLLDIFIEMEKRVILGEGKLDILKRVCAQINKSLLKI.INDYEEFS
Mch4       145 .TEMTSLSFLAFLEKQGKIDEDNLTCLEDLCKTVVPKLLRN.IEKYKR.E FLAME-1    176 QGAGTSYRNVLQAAIQKSLKDPSNNFRSIPEER..........YKMKSK
Mch5-beta  183 KGEELCGVMTISDSPR...EQDSE...SQTLDK..........VYQMKSK
Mch4       192 KAIQIVTPPVDKEAES...YQGEEELVSQTDVKTFLEALPRAAVYRMNRN ↓CGVRGPAGGQQP
FLAME-1    215 PLGICLII....................DCIGNETELLRDTFTSLGYEV
Mch5-beta  217 PRGYCLIINMHNFAKAREKVPKLHSIRDRNGTELDAGALTTTFEELHFEI
Mch4       239 HRGLCVIVMMHSFT..........SLKDRQGTHKDAEILSHVFQWLGFTV
                                         b LGGGWASDEECGIQGSEARAVHSSPRS*
FLAME-1    244 QKFLHLSMHGISQILGQFACMPEHRDYDSFVCVLVSRGGSQSVYGVDQTH
Mch5-beta  267 KPEHDCT.VEQIYEILKIYQLMDHSNMDCFICCILSHGDKGIIYGTDGQE
Mch4       279 HIENNVTKVEMEMVLQKQKCNPAHADGDCFVFCILTHGRFGAVYSSDEAL
                                                     cc FLAME-1    294 SGLPLHHIRRMFMGDSCPYLAGKPKMFFIQNYVVSEGQLEDSSLLEVDGP
Mch5-beta  316 ..APIYELTSQFTGLKCPSLAGKPKVFFIQACQGDNYQKGIPVETDS..E
Mch4       329 ..IPIREIMSHFTALQCPRLAEKPKLFFIQACQGEEIQPSVSIEADALNP
                                         b c FLAME-1    344 AMKNVEFKAQKRGLCTVHREADFFWSLCTADMSLLEQSHSSPSLYLQCLS
Mch5-beta  362 EQPYLEMDLSSPQTRYIPDEADFLLGMATVNNCVSYRNPAEGTWYIQSLC
Mch4       377 EQAPTSLQDS......IPAEADFLLGLATVPGYVSFRHVEEGSWYIQSLC
                                                 b         b FLAME-1    394 QKLRQ..ERKRPLLDLHIELNGYMYDWNSRVSAKEKYYVWLQHTLRKKLI
Mch5-beta  412 QSLRERCPRGDDILTILTEVMYEVSNKDDKKNMG.KQMPQPTFTLRKKLV
Mch4       421 NHLKKLVPRHEDILSILTAVMDDVSRRVDKQGTK.KQMPQPAFTLRKKLV FLAME-1    442 LSYT......
Mch5-beta  461 FPSD......
Mch4       470 FPVPLDALSI
```

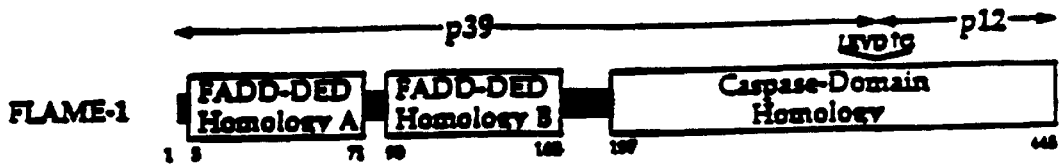

FIGURE 1B

```
  1 MAGLKRRASQVWPEEHGEQEHGLYSLHRMFDIVGTHLTHRDVRVLSFLFV
 51 DVIDDHERGLIRNGRDFLLALERQGRCDESNFRQVLQLLRIITRHDLLPY
101 VTLKRRAVCPDLVDKYLEETSIRYVTPRALSDPEPRPPQPSKTVPPHYP
151 VVCCPTSGPQMCSKRPARGRATLGSQRKRRKSVTPDPKEKQTCDIRLRVR
201 AEYCQHETALQGNVFSNKQDPLERQFERFNQANTILKSRDLGSIICDIKF
251 SELTYLDAFWRDYINGSLLEALKGVFITDSLKQAVGHEAIKLLVNVDEED
301 YELGRQKLLRNLMLQALP
```

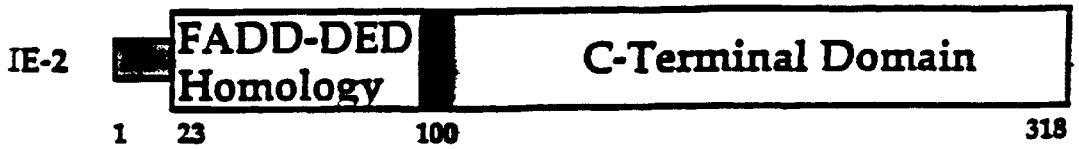

FIGURE 1C

```
1   MAGLKRRASQVWPEEHGEQEHGLYSLHRMFDIVGTHLTHRDVRVLSFLFV
1   .........................MD.FSRNLYDIGEQLDSEDLASLKFLSL
1   .........................MDPFLVLLHSVSSSLSSSELTELKFLCL

51  DVIDDHERGLIRNGRDFLLALERQGRCDESNFRQVLQLLRIITREDLLPYV
28  DYIPQRKQEPIKDALMLFQRLQEKRMLEESNLSFLKELLFRINRLDLLITY
29  GRVGKRKLERVQSGLDLFSMLLEQNDLEPGHTELLRELLASLRREDLLRRV
```

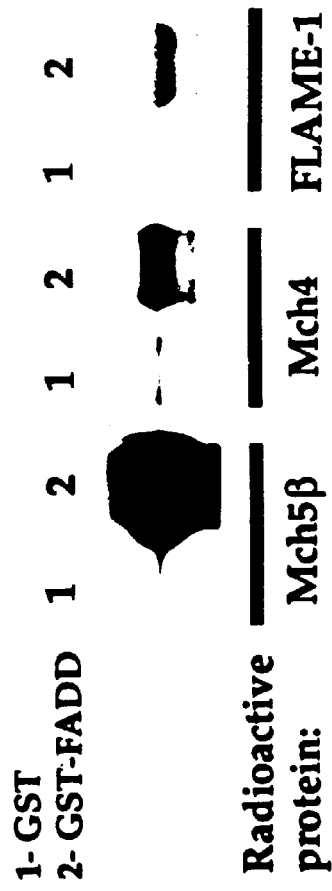
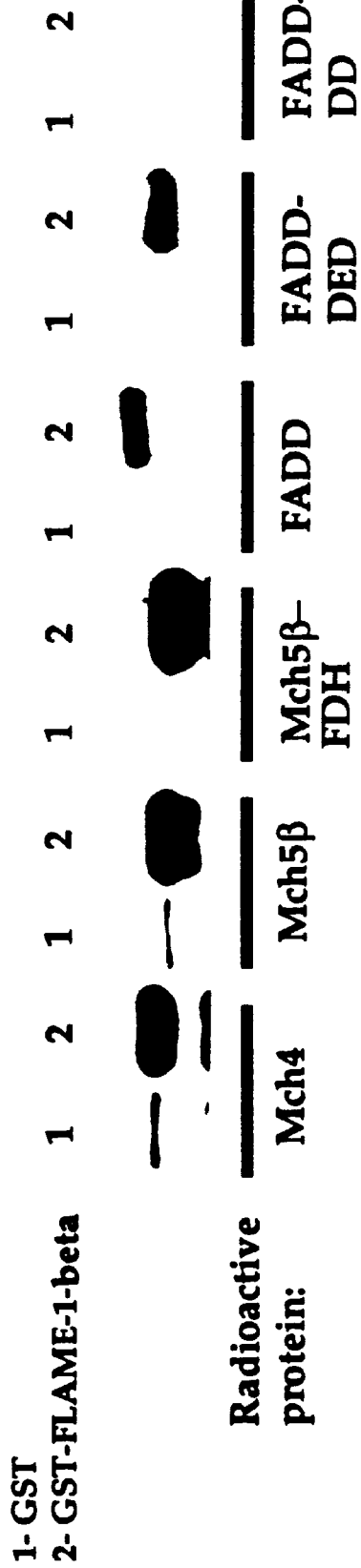

FIG. 2D

1 - GST
2 - GST-FLAME-1-CDH

Radioactive protein: Mch4, Mch5β

FIG. 2E

1 - GST
2 - GST-FLAME-2

Radioactive protein: FLAME-1, Mch4, Mch5β, FADD

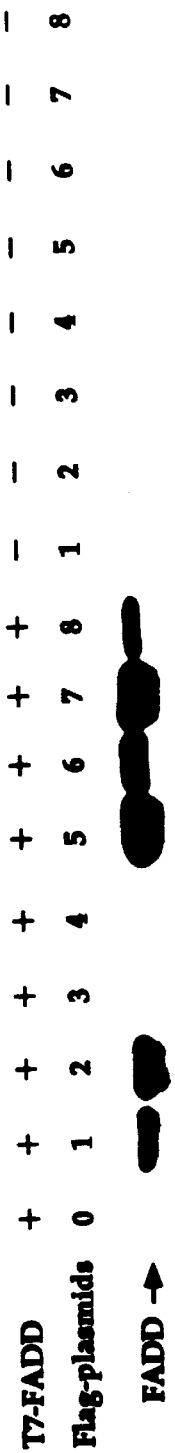
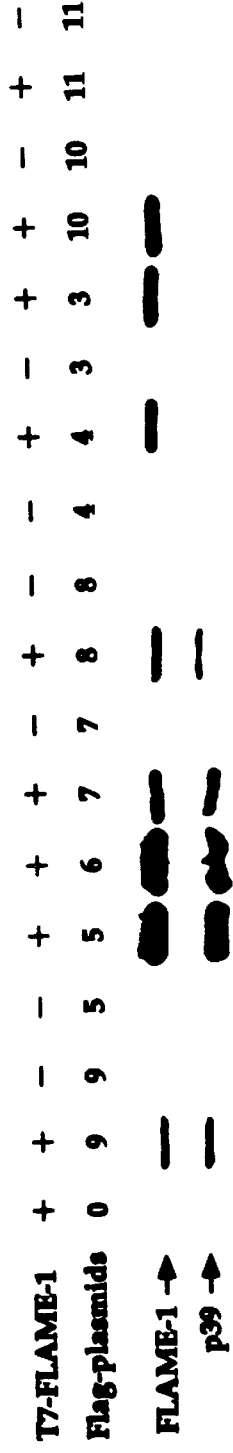
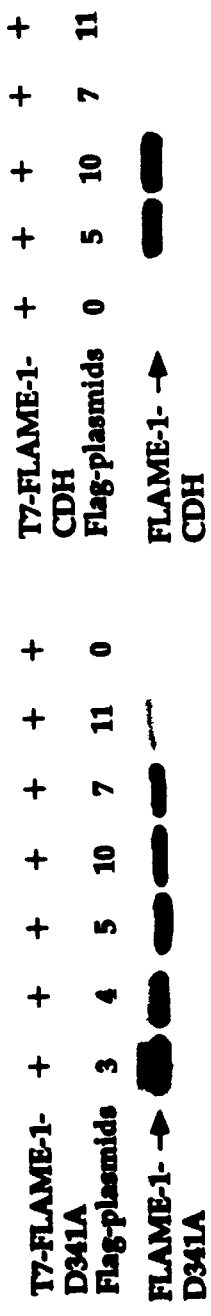
FIG.3A
FIG.3B
FIG.3C
FIG.3D

FIG. 3E

| T7-FLAME-2 | + | + | + |
|---|---|---|---|
| Flag-plasmids | 0 | 7 | 5 |

FLAME-2 →

FIG. 3F

| Flag-Fas | + | − | + | + | + | + | − | + | + | − |
|---|---|---|---|---|---|---|---|---|---|---|
| T7-FADD | − | + | + | + | + | + | − | − | + | − |
| T7-FLAME-1 | − | − | − | + | − | − | + | − | − | − |
| T7-FLAME-1-D341A | − | − | − | − | + | + | − | − | − | − |
| T7-FLAME-2 | − | − | − | − | − | − | − | + | + | + |

FLAME-1 →
p39 →
FADD →

FADD-LIKE ANTI-APOPTOTIC MOLECULES, METHODS OF USING THE SAME, AND COMPOSITIONS FOR AND METHODS OF MAKING THE SAME

This Application is a divisional of application Ser. No. 08/859,167, filed May 20, 1997, which issued as U.S. Pat. No. 6,037,461.

ACKNOWLEDGEMENT OF GOVERNMENT RIGHTS

This invention was made with Government support under Grant AG 13487 from the National Institutes of Health. The Government has certain rights in this invention.

FIELD OF THE INVENTION

The invention relates to the identification and cloning of two FADD-like anti-apoptotic molecules that regulate Fas/TNFR1- or UV-induced apoptosis, to methods of using the same, and to compositions for and methods of making the same and to methods of making and using the same.

BACKGROUND OF THE INVENTION

Apoptotic cell death is essential for normal development and maintenance of normal tissue size homeostasis in multicellular organisms. There is growing evidence that dysregulation of apoptosis may lead to several human diseases including cancer and degenerative neuronal diseases such as Alzheimer's and Parkinson's diseases.

Several members of the caspase family of proteases (Alnemri, E.S. et al. 1996 Cell 87, 171, which is incorporated herein by reference) have been implicated as key regulators of programmed cell death or apoptosis (Alnemri, E.S. 1997 J. Cell. Biochem. 64, 33–42 and Henkart, P. A. 1996 Immunity 4, 195–201 which are incorporated herein be reference). The pro-apoptotic caspases can be divided into two groups: those with a large prodomain such as ICH-1 (caspase-2), Mch4 (caspase-10), Mch5/MACH/FLICE (caspase-8) and Mch6/ICE-Lap-6 (caspase-9) and those with a small prodomain such as CPP32/YAMA/Apopain (caspase-3), Mch2 (caspase-6) and Mch3/ICE-Lap-3 (caspase-7). Caspases with large prodomains are probably the most upstream caspases. They are recruited by several death-signaling receptors that belong to the TNFR family, through interactions of their prodomain with the receptor-interacting adaptor molecules FADD/Mort1 or CRADD/RAIDD. For example, the prodomains of Mch4 and Mch5 contain two tandem regions that show significant homology with the N-terminal death effector domain (DED) of FADD. Engagement of Fas/TNFR1 results in recruitment of FADD to the receptor complex, which presumably triggers activation of the caspase apoptotic pathway through interaction of its DED with the corresponding motifs in the prodomain of Mch5 and probably Mch4. CRADD presumably functions like FADD by recruiting ICH-1 to the Fas/TNFR1 complex, through interaction of its N-terminal domain with the corresponding motif in the prodomain of ICH-1. Thus, the prodomains of caspases function to physically link the death receptors to the downstream caspase activation pathway.

There is a need to identify proteins that regulate apoptosis. There is a need for isolated FADD-like anti-apoptotic molecules that regulate Fas/TNFR1- or UV-induced apoptosis, and for compositions and methods of producing and isolating FADD-like anti-apoptotic molecules that regulate Fas/TNFR1- or UV-induced apoptosis. There is a need to isolated proteins that are FADD-like anti-apoptotic molecules that regulate Fas/TNFR1- or UV-induced apoptosis. There is a need to isolated nucleic acid molecules that encode FADD-like anti-apoptotic molecules that regulate Fas/TNFR1- or UV-induced apoptosis. There is a need for compounds which inhibit activity of FADD-like anti-apoptotic molecules that regulate Fas/TNFR1- or UV-induced apoptosis. There is a need for kits and methods of identifying such compounds.

SUMMARY OF THE INVENTION

The invention relates to substantially pure proteins that have amino acid sequences shown in SEQ ID NO:2 or SEQ ID NO:4.

The invention relates to pharmaceutical compositions comprising a protein that has the amino acid sequence shown in SEQ ID NO:2 or SEQ ID NO:4 in combination with a pharmaceutically acceptable carrier.

The invention relates to isolated nucleic acid molecules that comprise nucleic acid sequences that encode a protein that has an amino acid sequence shown in SEQ ID NO:2 or SEQ ID NO:4.

The invention relates to pharmaceutical compositions that comprise nucleic acid molecule that comprise nucleic acid sequences that encode a protein that has an amino acid sequence shown in SEQ ID NO:2 or SEQ ID NO:4 in combination with a pharmaceutically acceptable carrier.

The invention relates to isolated nucleic acid molecules that consist of SEQ ID NO:1 or SEQ ID NO:3 or a fragment thereof having at least 5 nucleotides.

The invention relates to a recombinant expression vector comprising the nucleic acid molecule that has a nucleotide sequence that comprises SEQ ID NO:1 or SEQ ID NO:3.

The invention relates to a host cell comprising a recombinant expression vector comprising the nucleic acid molecule that has a nucleotide sequence that comprises SEQ ID NO:1 or SEQ ID NO:3.

The invention relates to an oligonucleotide molecule comprising a nucleotide sequence complimentary to a nucleotide sequence of at least 5 nucleotides of SEQ ID NO:1 or SEQ ID NO:3.

The invention relates to isolated antibodies that bind to an epitope on SEQ ID NO:2 and/or SEQ ID NO:4.

The invention relates to methods of identifying substrates, activators or inhibitors of FLAME-1 and/or FLAME-2.

The invention relates to methods of inhibiting expression of FLAME-1 and/or FLAME-2 by contacting cells that express FLAME-1 and/or FLAME-2 with a nucleic acid molecule that comprises an antisense nucleotide sequence that prevents transcription of FLAME-1 and/or FLAME-2 gene sequences or translation of FLAME-1 and/or FLAME-2 mRNA.

BRIEF DESCRIPTION OF THE FIGURES

FIGS. 1A–1F disclose sequence analysis, tissue distribution and chromosomal localization data of FLAMEs. FIG. 1A shows the predicted amino acid sequence of FLAME-1 compared to Mch5-beta and Mch4 and FLAME-1's structure. FIG. 1B shows the predicted amino acid sequence of FLAME-2 and its structure. FIG. 1C shows the N-terminal region of FLAME-2 (amino acids 23–101) shares significant homology with the FDH-A of Mch5b and the N-terminal DED of FADD. FIG. 1D shows results from Northern blot analysis of FLAME-1 and FLAME-2 mRNAs. FIG. 1E shows FLAME-1, Mch4 and Mch5 genes are localized to chromosome 2q33–34.

FIGS. 2A–2E shows in vitro interactions of FLAME-1 and FLAME-2. FIG. 2A shows cleavage of FLAME-1 by caspases. FIGS. 2B–2E show in vitro interactions.

FIGS. 3A–3F show in vivo interactions of FLAME-1 and FLAME-2.

DETAILED DESCRIPTION OF THE INVENTION

Figure 1D:
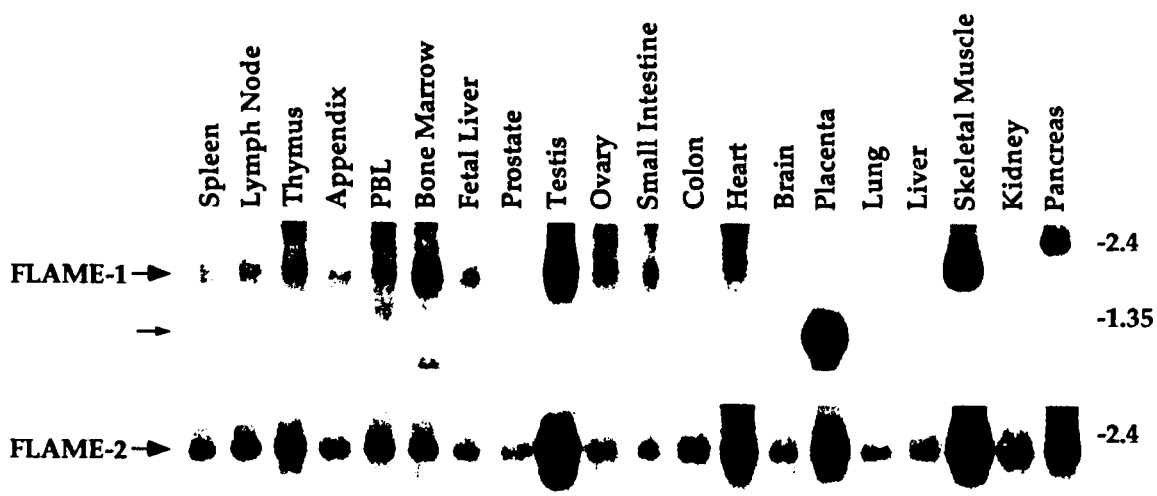

As used herein, the term "FLAMEs" is meant to refer to the two FADD-like apoptotic/anti-apoptotic molecules that have been isolated and cloned and discovered to regulate Fas/TNFR1- or UV-induced apoptosis.

As used herein, FLAME-1 refers to one of the two FLAMEs. The amino acid sequence of FLAME-1 is set forth in SEQ ID NO:2. The cloned cDNA which encodes FLAME-1 is set forth in SEQ ID NO:1.

As used herein, FLAME-2 refers to one of the two FLAMEs. The amino acid sequence of FLAME-2 is set forth in SEQ ID NO:4. The cloned cDNA which encodes FLAME-2 is set forth in SEQ ID NO:3.

Two novel human anti-apoptotic proteins that contain FADD/Mort1 DED-homology regions, designated FLAME-1 and FLAME-2 have been identified and cloned. FLAME-1, although most similar in structure to Mch4 and Mch5, does not possess caspase activity, but can interact specifically with FADD, Mch4, Mch5 and FLAME-2. FLAME-1 is recruited to the Fas receptor complex and can abrogate Fas/TNF-induced apoptosis upon expression in Fas/TNF-sensitive MCF-7 cells. FLAME-2, on the other hand, is similar in structure to FADD, but its C-terminal region does not have a death domain homology. It interacts weakly with Mch4 and Mch5 but does not interact with FADD. It can abrogate UV-induced apoptosis and to a lesser degree inhibit Fas/TNFR-induced apoptosis in the same cell line. These findings identify two novel endogenous control points that regulate Fas/TNFR1- and UV-mediated apoptosis.

The discovery of the two FLAMEs provides the means to design and discover specific inhibitors, activators and substrates of these anti-apoptotic molecules. According to the present invention, FLAMEs may be used to screen compounds for inhibitors, activators or substrates. Inhibitors are useful as apoptotic agents. Activators are useful as anti-apoptotic agents. FLAME-1 and FLAME-2 proteins are useful as reagents in assays to identify inhibitors and activators as well as in binding assays such as FLAME-1 binding assays with FADD, Mch4, Mch5 and FLAME-2 and FLAME-2 binding assays with Mch4, Mch5 and FLAME-1. FLAME-1 may also be useful as a substrate for caspase in assays to identify caspase inhibitors. Kits are provided for screening compounds for FLAMEs inhibitors. Kits are provided for screening compounds for FLAMEs activators. Kits are provided for screening compounds for FLAME binding assays. The nucleotide sequences that encode the FLAMEs are disclosed herein and allow for the production of pure protein, the design of probes which specifically hybridize to nucleic acid molecules that encode the FLAMEs and antisense compounds to inhibit transcription of FLAMEs. Anti-FLAME-1 and anti-FLAME-2 antibodies are provided. Anti-FLAME-1 antibodies may be inhibitors of FLAME-1 and may be used in methods of isolating pure FLAME-1 and methods of inhibiting FLAME-1 activity. Anti-FLAME-2 antibodies may be inhibitors of FLAME-2 and may be used in methods of isolating pure FLAME-2 and methods of inhibiting FLAME-1 activity.

The present invention provides substantially purified FLAMEs, FLAME-1 and FLAME-2 which have amino acid sequences consisting of: SEQ ID NO:2 and SEQ ID NO:4, respectively. FLAME-1 and FLAME-2 can be isolated from natural sources, produced by recombinant DNA methods or synthesized by standard protein synthesis techniques.

Antibodies which specifically bind to a particular FLAME may be used to purify the protein from natural sources using well known techniques and readily available starting materials. Such antibodies may also be used to purify the FLAME from material present when producing the protein by recombinant DNA methodology. The present invention relates to antibodies that bind to an epitope which is present on a FLAME selected from the group consisting of: FLAME-1—SEQ ID NO:2 and FLAME-2—SEQ ID NO:4. As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. In some embodiments, the antibodies specifically bind to an epitope of only one of: FLAME-1 and FLAME-2. Antibodies that bind to an epitope which is present on a FLAME are useful to isolate and purify the FLAME from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual,* Cold Spring Harbor Laboratory, Cold Spring Harbor, N.Y. which is incorporated herein by reference. Briefly, for example, the FLAME-1 or FLAME-2 protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the FLAME, the hybridoma which produces them is cultured to produce a continuous supply of antibodies.

Using standard techniques and readily available starting materials, a nucleic acid molecule that encodes each of the FLAMEs may be isolated from a cDNA library, using probes or primers which are designed using the nucleotide sequence information disclosed in SEQ ID NO:1 or SEQ ID NO:3. The present invention relates to an isolated nucleic acid molecule that comprises a nucleotide sequence that encodes a FLAME selected from the group consisting of FLAME-1 and FLAME-2 that comprises the amino acid sequence of SEQ ID NO:2 and SEQ ID NO:4, respectively. In some embodiments, the nucleic acid molecules consist of a nucleotide sequence that encodes FLAME-1 or FLAME-2. In some embodiments, the nucleic acid molecules comprise the nucleotide sequence that consists of the coding sequence in SEQ ID NO:1 or SEQ ID NO:3. In some embodiments, the nucleic acid molecules consist of the nucleotide sequence set forth in SEQ ID NO:1 or SEQ ID NO:3. The isolated nucleic acid molecules of the invention are useful to prepare constructs and recombinant expression systems for preparing the FLAMEs of the invention.

A cDNA library may be generated by well known techniques. A cDNA clone which contains one of the nucleotide sequences set out is identified using probes that comprise at least a portion of the nucleotide sequence disclosed in SEQ ID NO:1 or SEQ ID NO:3. The probes have at least 16 nucleotides, preferably 24 nucleotides. The probes are used to screen the cDNA library using standard hybridization techniques. Alternatively, genomic clones may be isolated using genomic DNA from any human cell as a starting material. In either cDNA or genomic probes, the sequence of the probe is unique to the FLAME that it is designed to hybridize to. That is, the sequence is selected to be unique relative to other known sequences. Unique sequences may be identified by comparing the sequences set forth in SEQ ID NO:1 and SEQ ID NO:3 to each other and to the sequences set forth in sequence data bases such as Genbank. Unique fragments of SEQ ID NO:1 and SEQ ID NO:3 are useful because they can hybridize to clones without cross hybridizing to other non-FLAME encoding sequences.

The present invention relates to isolated nucleic acid molecules that comprise a nucleotide sequence identical or complementary to a unique fragment of SEQ ID NO:1 or SEQ ID NO:3 which is at least 10 nucleotides. In some embodiments, the isolated nucleic acid molecules consist of a unique nucleotide sequence identical or complementary to a fragment of SEQ ID NO:1 or SEQ ID NO:3 which is at least 10 nucleotides. In some embodiments, the isolated nucleic acid molecules comprise or consist of a nucleotide sequence identical or complementary to a unique fragment of SEQ ID NO:1 or SEQ ID NO:2 which is 15–150 nucleotides. In some embodiments, the isolated nucleic acid molecules comprise or consist of a nucleotide sequence identical or complementary to a unique fragment of SEQ ID NO:1 or SEQ ID NO:3 which is 15–30 nucleotides. Isolated nucleic acid molecules that comprise or consist of a nucleotide sequence identical or complementary to a fragment of SEQ ID NO:1 or SEQ ID NO:3 which is at least 10 nucleotides are useful as probes for identifying genes and cDNA sequence having SEQ ID NO:1 or SEQ ID NO:3, respectively, PCR primers for amplifying genes and cDNA having SEQ ID NO:1 or SEQ ID NO:3, respectively, and antisense molecules for inhibiting transcription and translation of genes and CDNA, respectively, which encode FLAMEs having the amino acid sequence of SEQ ID NO:2 or SEQ ID NO:4, respectively.

The cDNA that encodes FLAME-1 or FLAME-2 may be used as a molecular marker in electrophoresis assays in which cDNA from a sample is separated on an electrophoresis gel and FLAME probes are used to identify bands which hybridize to such probes. Specifically, SEQ ID NO:1 or portions thereof, or SEQ ID NO:3 or portions thereof, may be used as a molecular marker in electrophoresis assays in which cDNA from a sample is separated on an electrophoresis gel and FLAME-specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes FLAME-1 and FLAME-2, respectively. Electrophoresis gels useful in such an assay include standard polyacrylamide gels as described in Sambrook et al., Molecular Cloning a Laboratory Manual, Second Ed. Cold Spring Harbor Press (1989) which is incorporated herein by reference.

The nucleotide sequences in SEQ ID NO:1 and SEQ ID NO:3 may be used to design probes, primers and complimentary molecules which specifically hybridize to the unique nucleotide sequences of FLAME-1 and FLAME-2, respectively. Probes, primers and complimentary molecules which specifically hybridize to nucleotide sequence that encodes FLAME-1 and FLAME-2 may be designed routinely by those having ordinary skill in the art.

The present invention also includes labeled oligonucleotides which are useful as probes for performing oligonucleotide hybridization methods to identify FLAME-1 and FLAME-2. Accordingly, the present invention includes probes that can be labeled and hybridized to unique nucleotide sequences of FLAME-1 and FLAME-2. The labeled probes of the present invention are labeled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of FLAME-1 and FLAME-2.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encode FLAME-1 or FLAME-2 and insert it into an expression vector using standard techniques and readily available starting materials.

The present invention relates to a recombinant expression vector that comprises a nucleotide sequence that encodes FLAME-1 or FLAME-2 that comprises the amino acid sequence of SEQ ID NO:2 or SEQ ID NO:4, respectively. As used herein, the term "recombinant expression vector" is meant to refer to a plasmid, phage, viral particle or other vector which, when introduced into an appropriate host, contains the necessary genetic elements to direct expression of the coding sequence that encodes the FLAMEs of the invention. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1 or SEQ ID NO:3. The recombinant expression vectors of the invention are useful for transforming hosts to prepare recombinant expression systems for preparing the FLAMEs of the invention.

The present invention relates to a host cell that comprises the recombinant expression vector that includes a nucleotide sequence that encodes a FLAME that comprises SEQ ID NO:1 or SEQ ID NO:3. In some embodiments, the host cell comprises a recombinant expression vector that comprises SEQ ID NO:1 or SEQ ID NO:3. Host cells for use in well known recombinant expression systems for production of proteins are well known and readily available. Examples of host cells include bacteria cells such as *E. coli,* yeast cells such as *S. cerevisiae,* insect cells such as *S. frugiperda,* non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes a FLAME that comprises the amino acid sequence of SEQ ID NO:2 or SEQ ID NO:4. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes a FLAME of the invention is operably linked to a mammary cell specific promoter whereby the coding sequence is only expressed in mammary cells and the recombinant protein so expressed is recovered from the animal's milk. In some embodiments, the coding sequence that encodes a FLAME is SEQ ID NO:1 or SEQ ID NO:3.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in *E. coli.* The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce FLAME of the invention using routine techniques and readily available starting materials. (See e.g., Sambrook et al., *Molecular Cloning a Laboratory Manual,* Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual,* Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes a FLAME is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate the FLAME that is produced using such expression systems. The methods of purifying FLAMEs from natural sources using antibodies which specifically bind to the FLAME as described above, may be equally applied to purifying FLAMEs produced by recombinant DNA methodology.

Examples of genetic constructs include a FLAME coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes a FLAME from readily available starting materials. Such gene constructs are useful for the production of the FLAME.

In some embodiments of the invention, transgenic non-human animals are generated. The transgenic animals according to the invention contain SEQ ID NO:1 or SEQ ID NO:3 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the Mch2 isoform. Preferred animals are rodents, particularly goats, rats and mice.

In addition to producing these proteins by recombinant techniques, automated peptide synthesizers may also be employed to produce FLAMEs of the invention. Such techniques are well known to those having ordinary skill in the art and are useful if derivatives which have substitutions not provided for in DNA-encoded protein production.

FLAMEs may be used as a pharmaceutical to inhibit apoptosis. Similarly, nucleic acid molecules that encode FLAMEs may be used as part of pharmaceutical compositions for gene therapy. Diseases characterized by apoptosis include HIV infection and Alzheimer's disease. Those having ordinary skill in the art can readily identify individuals who are suspected of suffering from such diseases, conditions and disorders using standard diagnostic techniques.

Pharmaceutical compositions according to the invention comprise a pharmaceutically acceptable carrier in combination with FLAME-1 or FLAME-2, or a nucleic acid molecule that encodes FLAME-1 or FLAME-2. Pharmaceutical formulations are well known and pharmaceutical compositions comprising FLAME-1 or FLAME-2, or a nucleic acid molecule that encodes FLAME-1 or FLAME-2 may be routinely formulated by one having ordinary skill in the art. Suitable pharmaceutical carriers are described in *Remington's Pharmaceutical Sciences,* A. Osol, a standard reference text in this field, which is incorporated herein by reference. The present invention relates to an injectable pharmaceutical composition that comprises a pharmaceutically acceptable carrier and FLAME-1 or FLAME-2, or a nucleic acid molecule that encodes FLAME-1 or FLAME-2. Some embodiments of the invention relate to injectable pharmaceutical compositions that comprise a pharmaceutically acceptable carrier and amino acid sequence SEQ ID NO:2 or SEQ ID NO:4. FLAME-1 or FLAME-2 is preferably sterile and combined with a sterile pharmaceutical carrier.

In some embodiments, for example, FLAME-1 or FLAME-2 can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise FLAME-1 or FLAME-2 in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

Nucleic acid molecules that encode FLAME-1 or FLAME-2 may be delivered using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto.

In one embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions.

In another embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another embodiment of the present invention, nucleic acid is delivered through folate receptor means. The nucleic acid sequence to be delivered to a cell is linked to polylysine and the complex is delivered to cells by means of the folate receptor. U.S. Pat. No. 5,108,921 issued Apr. 28, 1992 to Low et al., which is incorporated herein by reference, describes such delivery components.

Pharmaceutical compositions according to the invention include delivery components in combination with nucleic acid molecules that encode FLAME-1 or FLAME-2 which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention.

The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

According to one aspect of the invention, compounds may be screened to identify FLAME-1 or FLAME-2 inhibitors, activators or compounds that interfere with or disrupt FLAME-1 or FLAME-2 interactions with Fas, TNFR1, FADD, Mch4 and Mch5. Inhibitors of FLAME-1 or FLAME-2 are useful as apoptotic agents. Activators of FLAME-1 or FLAME-2 are useful as anti-apoptotic agents.

Ware, C. F. et al. 1996 J. Cell. Biochem. 60(1):47–55, Nagata S. 1997 Cell 88(3):355–65, Nagata S. 1996 *Adv Exp Med Biol.* 406:119–24, Nagata S. and P. Golstein 1995 Science 267(5203):1449–56, Nagata S. 1994 Adv Immunol. 57:129–44, and Lu, M. L. et al. 1996 Proc. Natl. Acad. Sci. USA 93(17):8977–82, which are each incorporated herein by reference each describe Fas/TNFR1-induced apoptosis.

Nagata, S. 1997 Cell 88, 355–365 Rosette, C. and M. Karin, 1996 Science 274, 1194–1197, which are both incorporated herein by reference each describe UV-induced apoptosis.

Inhibitors of FLAME-1 or FLAME-2 are useful as apoptic agents may be identified by screening compounds to ascertain their effect on the anti-apoptosis activity of FLAME-1 or FLAME-2, respectively. In some embodiments of the invention, compounds are screened to identify inhibitors by delivering FLAME-1 or FLAME-2 to cells in the presence or absence of a test compound. Under assay conditions, the FLAME will have an anti-apoptotic effect on the cells in the absence of test compound. If in the presence of the test compound, the cells become apoptotic, the test compound is candidate inhibitor of the FLAME. Antibodies which inhibit FLAME activity are useful as inhibitors and, therefore as positive controls in the assay. In some embodiments, the FLAME is delivered to the cell as a protein. In some embodiments, the FLAME is delivered to the cell as a nucleic acid molecule that encodes the protein. In some embodiments of the invention, compounds are screened to identify inhibitors by contacting the FLAME with a caspase molecule known to bind to the FLAME. The molecules are contacted in the presence or absence of a test compound. Under assay conditions, the binding of the molecules in the absence of test compound but not in the presence of the compound indicates that the compound inhibits caspase/FLAME binding. Those having ordinary skill in the art can readily detect whether or not caspase and FLAME molecules are bound to each other. Antibodies can inhibit FLAMEs from binding to caspase.

Activators of FLAME-1 or FLAME-2 are useful as anti-poptotic agents may be identified by screening compounds to ascertain their effect on the anti-apoptosis activity of FLAME-1 or FLAME-2, respectively. In some embodiments of the invention, compounds are screened to identify activators by delivering FLAME-1 or FLAME-2 to cells in the presence or absence of a test compound. Under assay conditions, the cells will be apoptotic in the absence of test compound. If in the presence of the test compound, the cells cease being apoptotic, the test compound is candidate activator of the FLAME. In some embodiments, the FLAME is delivered to the cell as a protein. In some embodiments, the FLAME is delivered to the cell as a nucleic acid molecule that encodes the protein.

The invention provides assays for screening compounds to identify and evaluating compounds that disrupt or interfere with FLAME interactions with each other as well as Fas, FADD, TNFR1, Mch4 and Mch5 molecules. Assays are provided for identifying compounds that inhibit FLAME-1 or FLAME-2 binding to FADD, Mch4, Mch5, TNFR1 or Fas, comprising the steps of performing a test assay by contacting the FLAME with Fas, FADD, TNFR1, Mch4 or Mch5 in the presence of a test compound under conditions in which the FLAME binds to the Fas, FADD, TNFR1, Mch4 or Mch5 in the absence of the test compound and determining whether the FLAME binds to the Fas, FADD, TNFR1, Mch4 or Mch5. Assays are provided for identifying compounds that inhibit FLAME-1 binding to FLAME-2 comprising the steps of performing a test assay by contacting the FLAME-1 with FLAME-2 in the presence of a test compound under conditions in which the FLAME-1 binds to the FLAME-2 in the absence of the test compound and determining whether the FLAME-1 binds to the FLAME-2.

In some embodiments of the invention, the preferred concentration of test compound is between 1 $\mu$M and 500 $\mu$M. A referred concentration is 10 $\mu$M to 100 $\mu$M. In some preferred embodiments, it is desirable to use a series of dilutions of test compounds.

Kits are included which comprise containers with reagents necessary to screen test compounds. Such kits include FLAME-1 or FLAME-2 and/or a nucleic acid molecule that encodes FLAME-1 or FLAME-2 and instructions for performing the assay. Kits may include cells, and may optionally include antibodies as a control.

According to another aspect of the invention, transgenic animals, particularly transgenic mice, are generated. In some embodiments, the transgenic animals according to the invention contain a nucleic acid molecule which encodes FLAME-1 or FLAME-2. Such transgenic mice may be used as animal models for studying overexpression of FLAME-1 or FLAME-2 and for use in drug evaluation and discovery efforts to find compounds effective to inhibit or modulate the activity of FLAME-1 or FLAME-2. One having ordinary skill in the art using standard techniques, such as those taught in U.S. Pat. No. 4,873,191 issued Oct. 10, 1989 Wagner and U.S. Pat. No. 4,736,866 issued Apr. 12, 1988 to Leder, both of which are incorporated herein by reference, can produce transgenic animals which produce the FLAME-1 or FLAME-2 and use the animals in drug evaluation and discovery projects.

Another aspect of the present invention relates to knockout mice and methods of using the same. In particular, transgenic mice may be generated which are homozygous for a mutated, non-functional FLAME-1 and/or FLAME-2 gene which is introduced into them using well known techniques. The mice produce no functional FLAME-1 and/or FLAME-2 and are useful to study the function of FLAME-1 and/or FLAME-2. Furthermore, the mice may be used in assays to study the effect of test compounds on FLAME deficiency. The FLAME deficient mice can be used to determine if, how and to what extent FLAME inhibitors will effect the animal and thereby address concerns associated with inhibiting the activity of the molecule.

Methods of generating genetically deficient "knock out" mice are well known and disclosed in Capecchi, M. R. (1989) Science 244:1288–1292 and Li, P. et al. (1995) CELL 80:401–411, which are each incorporated herein by reference. The human FLAME cDNA clone or the murine FLAME cDNA clone such as the murine FLAME-2 cDNA set forth in SEQ ID NO:5 can be used to isolate a murine FLAME genomic clone. The genomic clone can be used to prepare a FLAME targeting construct which can disrupt the FLAME gene in the mouse by homologous recombination.

The targeting construct contains a non-functioning portion of the FLAME gene which inserts in place of the functioning portion of the native mouse gene. The non-functioning insert generally contains an insertion in the exon that encodes the active region of FLAME-1 or FLAME-2. The targeting construct can contain markers for both positive and negative selection. The positive selection marker allows for the selective elimination of cells without it while the negative selection marker allows for the elimination of cells that carry it.

For example, a first selectable marker is a positive marker that will allow for the survival of cells carrying it. In some embodiments, the first selectable marker is an antibiotic resistance gene such as the neomycin resistance gene can be placed within the coding sequences of the Mch2 gene to render it non-functional while additionally rendering the construct selectable. The antibiotic resistance gene is within the homologous region which can recombine with native sequences. Thus, upon homologous reconstruction, the non-functional and antibiotic resistance selectable gene sequences will be taken up.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Clones are then injected into the blastocysts and implanted into pseudopregnant females. Chimeric offspring which are capable of transferring the recombinant genes in their germline are selected, mated and their offspring is examined for heterozygous carriers of the recombined genes. Mating of the heterozygous offspring can then be used to generate fully homozygous offspring which are the FLAME-deficient knock out mouse.

The present invention relates to methods of and compositions for inhibiting the expression of FLAME-1 or FLAME-2 in cells. In one embodiment, antisense oligonucleotides are provided which have a nucleotide sequence complementary to a nucleotide sequence of mRNA that encodes FLAME-1 or FLAME-2.

The antisense oligonucleotides of the present invention comprise sequences complementary to regions of FLAME-1 or FLAME-2 mRNA. The oligonucleotides comprise a sequence complementary to a region selected from the sequence of the FLAME mRNA. The antisense oligonucleotides include single stranded DNA sequence and an antisense RNA oligonucleotide produced from an expression vector. Each of the antisense oligonucleotides of the present invention are complementary to regions of the FLAME mRNA sequence.

The antisense oligonucleotides of the present invention comprises a sequence complementary to a fragment of SEQ ID NO:1 or SEQ ID NO:3. See Ullrich et al., *EMBO J.*, 1986, 5:2503, which is incorporated herein by reference. Contemplated by this definition are fragments of oligos within the coding sequence for FLAME-1 or FLAME-2. Oligonucleotides are preferably complementary to a nucleotide sequence that is 5–50 nucleotides in length, in some embodiments 8–40, more preferably 12–25 nucleotides, in some embodiments 10–15 nucleotides and in some embodiments 12–20 nucleotides.

In addition, mismatches within the sequences identified above, which achieve the methods of the invention, such that the mismatched sequences are substantially complementary to the FLAME sequences are also considered within the scope of the disclosure. Mismatches which permit substantial complementarily to the FLAME sequences will be known to those of skill in the art once armed with the present disclosure. The oligos may also be unmodified or modified.

The present invention is also directed to a method of inhibiting FLAME-1 or FLAME-2 expression in mammals comprising contacting the mammal with an effective amount of an antisense oligonucleotide having a sequence which is complementary to a region of the FLAME-1 mRNA or FLAME-2 mRNA, respectively.

Methods of administering the antisense oligos of the present invention include techniques well known in the art such as and not limited to liposomes, plasmid expression, or viral vector including retroviral vectors. In the administration of oligos via vectors or plasmids, a non-coding RNA strand of FLAME is preferably used in order to produce antisense RNA oligos which are expressed by the cell. The RNA oligos then bind FLAME sense or coding RNA sequence.

Methods of administering the oligos to mammals include liposomes, and may be in a mixture with a pharmaceutically-acceptable carrier, selected with regard to the intended route of administration and the standard pharmaceutical practice. In addition, antibodies, ligands and the like may be incorporated into the liposomes thereby providing various modes of inhibiting FLAME expression. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton Pa.

The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty $\mu$g/ml antisense oligo was used for in vitro methods of providing oligos in media for cell growth in culture. This concentration may be extrapolated for in vivo use. The concentration of antisense oligonucleotides for in vivo use is about 40 $\mu$/g body weight. The in vivo use of the expression vector expressing RNA oligonucleotides is determined by the number of transfected cells.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use, the antisense oligonucleotides may be administered intravenously.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.*, 1986, 859, 88–94.

EXAMPLE

In order to characterize novel FADD-like apoptotic/anti-apoptotic molecules (FLAMEs) that interact with caspases, the Genbank expressed sequence tags (ESTs) data base was searched for sequences that are homologous to the FADD-like caspases Mch4 (caspase-10) and Mch5/MACH/FLICE (caspase-8) (Fernandes-Alnemri, T. et al., 1996 Proc. Natl. Acad. Sci. USA. 93, 7464–7469, Boldin, M. P. 1996 Cell 85, 803–815, and Muzio, M. et al. 1996 Cell 85, 817–827, which are each incorporated herein by reference). Two ESTs (clones 427786 and 576731) with statistically significant similarity to Mch5 (p<0.001) were identified. The 5' sequence of EST clone 427786 suggested that it is a 5'-truncated complementary DNA (cDNA) clone. PCR primers were synthesized and used to amplify a partial cDNA probe. The full length FLAME-1 cDNA was cloned from human Jurkat Uni-ZAP XR cDNA library (Fernandes-Alnemri, T. et al. 1994 J. Biol. Chem. 269, 30761, which is incorporated herein by reference) by screening the library with a partial FLAME-1 cDNA probe. The probe was amplified from Jurkat cDNA library by two PCR amplification steps using FLAME-1 specific primers derived from the 3' (Genbank accession # aa002262, which is incorporated herein by reference) and 5' (Genbank accession # aa001257, which is incorporated herein by reference) sequences of human EST clone 427786. The primary PCR was done with Mchx-pr1 (AGGCTGGTCTCGAACTCC—SEQ ID NO:7) and Mchx-pr3 (TTCTCCAAGCAGCAATCC—SEQ ID NO:8). The secondary PCR was done with Mchx-pr2 (GGCCTCCCAAAGTGCTGG—SEQ ID NO:9) and Mchx-pr4 (TTCAGGCTCCATAATGGG—SEQ ID NO:10). The PCR product was cloned into Sma I site of pBluescript II KS+ vector and then used to screen the Jurkat cDNA library. The beta-isoform of FLAME-1 was cloned by RT-PCR.

This probe was used to isolate and clone the full length cDNA (~1.9 kb) from a human Jurkat cDNA library, that encodes a novel protein (designated FLAME-1) of 445 amino acids with predicted relative molecular mass of 51 kDa (SEQ ID NO: 1; FIG. 1A). FIG. 1A shows co-linear alignment of the predicted amino acid sequence of human FLAME-1 with proMch4 and proMch5b and a schematic diagram of its structure. Based on the crystal structure of ICE and CPP32, the residues marked with a (c) are involved in catalysis and those marked with a (b) are involved in binding the carboxylate side chain of the substrate P1 aspartate. The active site pentapeptide QACQG (SEQ ID NO:11) in Mch4 and Mch5 is boxed. The residues that are unique to FLAME-1b are underlined. The vertical arrow indicates the splice junction, after which FLAME-1b differs from FLAME-1.

FLAME-1 is most similar to the Mch4 and Mch5 caspases. It has three distinct homology regions: Two N-terminal tandem stretches of approximately 67–79 residues that are significantly homologous to the N-terminal DED (residues 1–79) of FADD, here referred to as FADD-DED homology A (FDH-A, residues 5–71) and B (FDH-B, residues 90–168) regions. FDH-A and FDH-B share 38% and 28% identity with the DED of FADD, respectively. The FDH regions share 28–33% identity with the corresponding regions in Mch4 and Mch5b. The FDH regions are followed by a stretch of 249 residues (residues 197–445) that is significantly homologous to the region which encodes the large and small subunits of known caspases, here referred to as the caspase-domain homology (CDH) region. Although this region shares approximately 27–31% identity with the corresponding regions in Mch4 and Mch5b, there are several differences. This region contains a QNYVV (SEQ ID NO:12) motif instead of the conserved active site motif QACXG (X=R,Q,G—SEQ ID NO:13, SEQ ID NO:11, SEQ ID NO:14, respectively), present in caspases. Also, only one (G281) out of the three residues involved in catalysis, and two (Q323 and S386) out of the four residues involved in binding the carboxylate side chain of the substrate P1 aspartate, are conserved. This region contains a potential caspase cleavage site (LEVD-G—SEQ ID NO:15) C-terminal to the QNYVV (SEQ ID NO:12) motif, that can be cleaved by caspases to generate two polypeptides (p39 and p12) corresponding to the large and small subunits of caspases. These observations suggest that FLAME-1 could be a protease with a different substrate specificity compared to caspases, or an enzymatically inactive protein. Because of the presence of CDH and FDH regions, FLAME-1 would be predicted to interact with caspases and/or other FDH-containing proteins. A naturally existing alternatively spliced isoform of FLAME-1 (FLAME-1b) lacking the entire CDH region was also identified by RT-PCR. This isoform shares residues 1–231 with FLAME-1 but has a 39 amino acid-long unique C-terminus.

Clone 576731 contained a consensus Kozak translation initiation ATG codon, preceded by a stop codon (12 bp upstream), characteristic of a full length cDNA clone of FLAME-2 (SEQ ID NO:3; FIG. 1B). FIG. 1B shows the predicted amino acid sequence of FLAME-2 and its structure. The IMAGE Consortium clone 576731, was characterized by automated sequencing and found to encode full length FLAME-2. This clone was then used to screen the EST data base to identify the human counterpart. Several human ESTs were identified and their sequence information was used to design primers corresponding to the first and last six amino acids of human FLAME-2. Human FLAME-2 was then cloned by PCR from Jurkat T-lymphocytes. A BLAST search of the EST data base identified several overlapping human and mouse clones encoding the same protein. The human and mouse cDNAs (~2.2 kb) encode a novel protein (designated FLAME-2) of 318 amino acids with predicted relative molecular mass of 37 kDa. The human and mouse counterparts (proteins) are 99.3% identical. The only difference between the human and mouse FLAME-2 counterparts are underlined in FIG. 1B (human/mouse, R/K, P/S, A/T).

FIG. 1C shows the N-terminal region of FLAME-2 (amino acids 23–101) shares significant homology with the FDH-A of Mch5b and the N-terminal DED of FADD. FLAME-2 has a similar organization to FADD. It has an N-terminal FDH region (residues 23–101) that shares ~22% identity with the FADD-DED region (residues 1–79) and 20–30% identity with the FDH regions of Mch4, Mch5 and FLAME-1. However, its C-terminal domain (CTD, residues 102–318) is unique in that it shares no significant homology with the CTD of FADD (also known as the death domain) or any other known proteins. The structure of FLAME-2 suggests that it could be an adaptor molecule for an as yet unidentified signaling complex.

To determine the distribution of FLAME-1 and 2, various tissue mRNA samples were subjected to Northern blot analysis. Tissue distribution analysis of FLAME-1 and FLAME-2 mRNAs was performed on Northern blots prepared by Clontech containing 2 μg/lane of poly A+ RNA. Radioactive riboprobes were prepared by using human FLAME-1-CDH or FLAME-2-FDH cDNAs as templates for SP6 RNA polymerase in the presence of [a32P] CTP. The blots were hybridized, washed and then visualized by autoradiography. Numbers on the right indicate kilobases. PBLs, peripheral blood leukocyte. As shown in FIG. 1D, FLAME-2 mRNA (~1.9 kb) is expressed mainly in testes and skeletal muscle. This message is less abundant in the other human tissues examined. However, a ~1.2 kb abundant message is expressed in the placenta, which could be an alternatively spliced isoform of FLAME-1 mRNA. FLAME-2 mRNA (~2.2 kb), on the other hand is more abundant than FLAME-1 mRNA. It is constitutively expressed in all the tissues examined with particularly high expression in testes, skeletal muscle, heart and placenta.

Figures 1E, 1F:
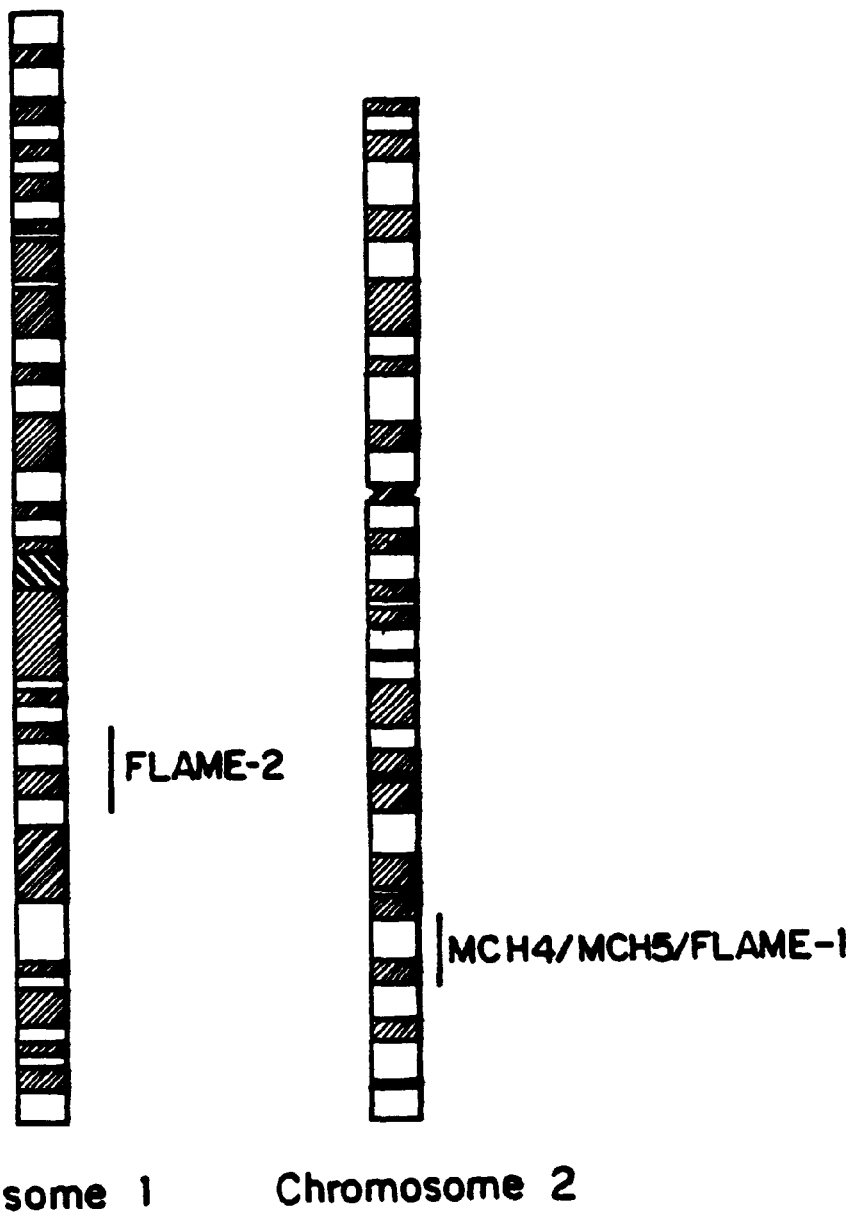

Chromosomal mapping linked the FLAME-1 and Mch5 genes to the D2S116 and D2S348 markers on chromosome 2q33–34 using radiation hybrid panels, in close proximity to where they were previously localized Mch4. The human genes for Mch5, FLAME-1 and FLAME-2 were mapped on a previously described rodent-human hybrid panels (Bullrich F. et al., 1995 Cancer Res. 55, 1199) and on the Genebridge 4 and Stanford G3 radiation hybrid panels (Research Genetics) using specific oligonucleotide primers. Radiation hybrid scoring data were submitted to the Whitehead Institute (WI) (http://www-genome.wi.mit.edu/cgi-bin/contig/rhmapper), and Stanford (http://shgc-www.stanford.edu) radiation hybrid servers. Data available through public databases and published genome maps (Chumakov I. et al., 1995 Nature 377.supp. 175) was then used to confirm the physical localization of markers and genes. As shown in FIG. 1E, FLAME-2 is localized to chromosome 1q23–24. This finding and the high degree of homology among their genes or gene products suggest that they might be descendents of a common ancestral gene through gene duplication. This finding is important because genetic lesions in this locus may have dramatic effects on Fas/TNFR1-induced apoptosis. The FLAME-2 gene was mapped to chromosome 1 within 6.51 cR of the CHLC.GATA43A04 marker in a 16 cM region between the D1S305 and D1S445 markers at 1q23–24.

To determine whether FLAME-1 possesses caspase activity, C-terminal His-tagged full length or truncated FLAME-1 lacking the FDH regions were expressed in bacteria or in the baculovirus expression system. Unlike Mch4 or Mch5, expression of these constructs did not result in cleavage of FLAME-1 (autoactivation) or generation of a caspase-like activity as determined with the tetrapeptide substrates YVAD-AMC (SEQ ID NO:16) or DEVD-AMC (SEQ ID NO:17), suggesting that FLAME-1 might be enzymatically inactive or possess an unknown enzymatic activity.

Figure 2A:
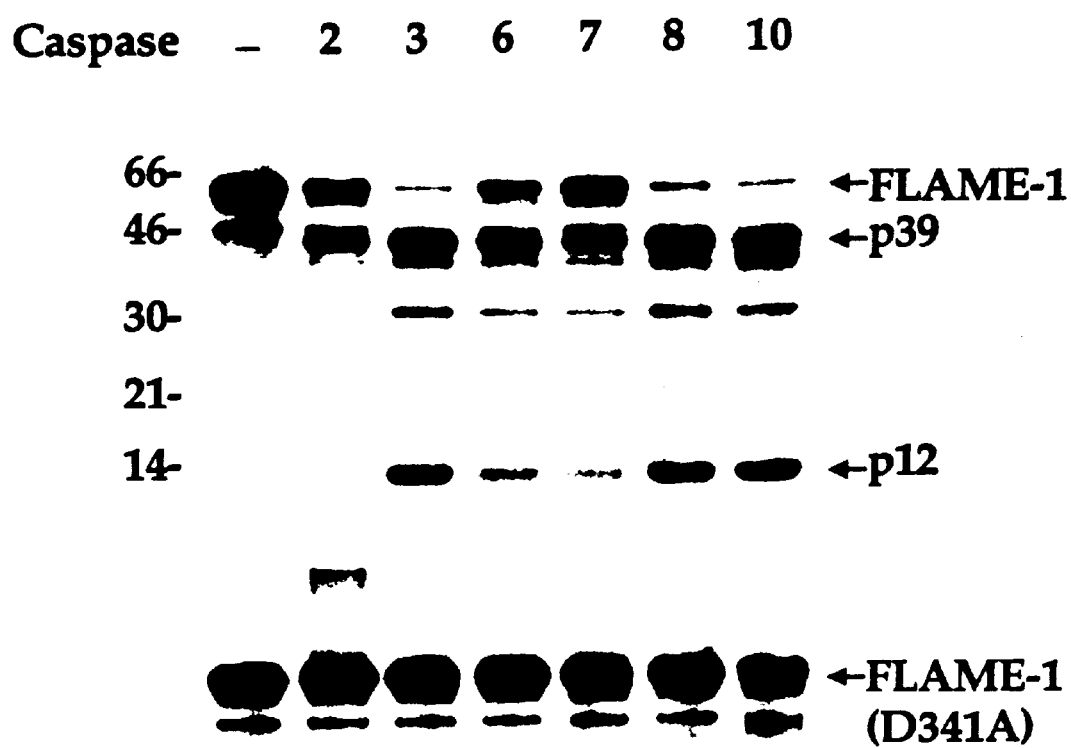

As shown in FIG. 2A, in vitro translated FLAME-1 can be cleaved by several caspases including CPP32, Mch2, Mch3, Mch4, Mch5 and ICH-1 to generate two fragments (p39 and p2) topologically equivalent to the large and small subunits of caspases. This cleavage occurs at Asp341 in the LEVD-G site, since a D to A mutation in this site prevents these caspases from cleaving FLAME-1. In the experiments shown in FIG. 2A, FLAME-1 or FLAME-1-D341A were 35S-labeled in vitro using Promega's TNT kit (Srinivasula, S. M. et al. 1996 Proc. Natl. Acad. Sci. USA. 93, 13706–13711 and Ahmad, M. et al. 1997 Cancer. Res. 57, 615–619). The labeled proteins were incubated with 100 ng of purified recombinant caspases and then analyzed as described before. In vitro translated FLAME-1 (upper panel) or FLAME-1-D341A (lower panel) were incubated without (lane 1) or with caspase-2 (ICH-1), caspase-3 (CPP32), caspase-6 (Mch2), caspase-7 (Mch3), caspase-8 (Mch5) or caspase-10 (Mch4) (lanes 2–7, respectively) for 1 h at 37° C. Proteins were then analyzed by SDS-PAGE and autoradiography. Full length FLAME-1, and its p39 and p12 fragments are indicated to the right.

Transfection studies showed that FLAME-1 may also be a caspase substrate in vivo. Expression of a T7-epitope tagged FLAME-1 (T7-FLAME-1) in 293 cells produced both full length and cleaved (p39) FLAME-1 (See FIGS. 3B and 3F). This cleavage was not observed with the D341A mutant FLAME-1 (T7-FLAME-1-D341A, see FIGS. 3C and 3F). Furthermore, stimulation of FLAME-1-transfected MCF7-FAS cells with anti-Fas antibody increased the amount of cleavage products. Thus, FLAME-1 appears to be a caspase target in apoptotic cells.

To investigate the participation of FLAME-1 and FLAME-2 in Fas/TNFR1 apoptotic signaling pathways, in vitro and in vivo binding studies and yeast-two hybrid analysis were performed and the data is shown in FIGS. 2B–2E. Radiolabeled FLAME-1, Mch4, Mch5b, FADD or mutants of these proteins were precipitated with various glutathione-S-transferase (GST) fusion proteins immobilized on glutathione-Sepharose beads. Contructs encoding GST fusion proteins were prepared using the bacterial expression vector pGEX-2T. The GST-fusion proteins were expressed in DH5a bacteria and then immobilized on glutathione-Sepharose. Labeled interacting proteins were prepared by in vitro transcription and translation in the presence of 35S-[methionine]. Following translation, equivalent amounts of the labeled proteins were incubated with various immobilized GST-fusion proteins. The beads were washed and boiled in SDS-sample buffer. The eluted proteins were resolved by SDS-PAGE and visualized by autoradiography. The indicated in vitro translated 35S-labeled proteins were precipitated with GST, (lanes 1b-e) or GST-FADD (lanes 2b), GST-FLAME-1-beta (lanes 2c), GST-FLAME-1-CDH (residues 196–445) (lanes 2d) or GST-FLAME-2 (lanes 2e) fusion proteins immobilized on glutathione-Sepharose beads. The bound proteins were then analyzed by SDS-PAGE and autoradiography. Truncated proteins FADD-DED or FADD-DD contain residues 1–79 or 80–205, respectively. The data in FIGS. 2B–2E shows that Mch4, Mch5b and FLAME-1 associated specifically with GST-FADD, although the interaction of FLAME-1 with FADD was weaker than that observed with Mch4 or Mch5b. FADD, FADD-DED, Mch4, Mch5b, and Mch5b-FDH, but not FADD-DD, also associated specifically with FLAME-1b (GST-FLAME-1-beta). These observations suggest that the interactions are mediated by the homologous FDH regions of these proteins. Mch5b but not Mch4 associated with a truncated FLAME-1 lacking its FDH regions (GST-FLAME-1-CDH), suggesting that the two proteins can also interact through their homologous CDH regions. GST-FLAME-2 associated strongly with FLAME-1 and weakly with Mch4 or Mch5b, but did not associate with FADD.

To demonstrate these interactions in vivo, 293 cells were transiently transfected with plasmids encoding T7-epitope tagged FADD, FLAME-1, FLAME-2 or mutants and various Flag epitope-tagged proteins. Because wild type Mch4, Mch5b and their CDH regions are potent inducers of apoptosis in 293 cells, active site Cys to Ala Flag-tagged mutants were used in these experiments to investigate their interactions with FLAME-1 and FLAME-2. FIGS. 3A–3F show FLAME-1 coimmunoprecipite with FADD, Mch4, Mch5b, and FLAME-2. 293 cells were transfected with expression plasmids encoding T7-epitope tagged FADD (FIG. 3A), FLAME-1 (FIG. 3B), FLAME-1-D341A (FIG. 3C), FLAME-1-CDH (residues 196–445) (FIG. 3D) or FLAME-2 (FIG. 3E), and different Flag-epitope tagged proteins as follows: 0, no Flag-plasmid; 1, FLAME-1; 2, FLAME-1b; 3, FLAME-2; 4, FLAME-2-FDH (residues 1–106); 5, Mch5b C345A; 6, Mch5b-FDH (residues 1–201); 7, Mch4 C358A; 8, Mch4-FDH (residues 18–189); 9, FADD; 10, Mch5b-CDH C345A (residues 201–464); 11, Mch4-CDH C358A (residues 200–479). A modified expression vector (T7-pcDNA3) encoding a T7-epitope tag under the CMV promoter was constructed by subcloning the T7-tag coding sequence of pET21b (Invitrogen) into the EcoRV site of pcDNA3. Epitope tagging was done by cloning cDNAs inframe into the multiple cloning sites of T7-pcDNA3 and/or the Flag plasmid pFLAG-CMV-2 (IBI Kodak). N-terminal and C-terminal deletion mutants were generated by PCR. Point mutants were generated by site directed mutagenesis using overlapping PCR mutagenic oligonucleotides. All PCR products were verified by sequencing. cDNAs of FLAME-1 or FLAME-2 without epitope tags were subcloned into pcDNA3. Flag-tagged Fas was constructed in pcDNA3. After 34–36 h, extracts were prepared and immunoprecipitated with a monoclonal antibody to the Flag-epitope. 293 or 293T human embryonic kidney cells were transiently transfected with the expression plasmids using the LipofectAMINE (Life Technologies)

method. Cells were lysed in a lysis buffer (50 mM Tris, pH 7.6, 150 mM NaCl, 0.1% NP-40) and incubated with anti Flag-M5 monoclonal antibody (IBI Kodak). The immune complexes were precipitated with protein-A/G-Sepharose, washed and then eluted by boiling in SDS-sample buffer. The eluted proteins were resolved by SDS-PAGE and detected by Western analysis with a HRP-conjugated T7-antibody (Novagen). The samples were analyzed by SDS-PAGE and Western blotted with a horseradish peroxidase (HRP)-conjugated T7-antibody. All extracts were immunoblotted with anti-Flag and anti-T7 to verify expression of the encoded proteins. FIG. 3F shows FLAME-1 is recruited to the Fas signaling complex. 293T cells were transfected with the indicated expression plasmids, immunoprecipitated and detected as in FIGS. 3A–3D.

Consistent with the in vitro results, T7-FADD coprecipitated with full length FLAME-1, Mch4 and Mch5b, or their isolated FDH regions, but not with FLAME-2 or FLAME-2-FDH (FIG. 3A). T7-FLAME-1 and its p39 fragment coprecipitated with full length FADD, Mch4, Mch5b or their isolated FDH regions (FIG. 3B). Full length T7-FLAME-1, but negligible amount of the p39 fragment, associated with Mch5-CDH, FLAME-2 or FLAME-2 FDH, suggesting that the entire CDH region of FLAME-1 is required for optimal interaction between these proteins. Similar results were obtained with T7-FLAME-1-D341A and T7-FLAME-1-CDH (FIGS. 3C and 3D). No interactions were observed between T7-FLAME-1b and Flag-Mch4-CDH or Flag-Mch5b-CDH, suggesting that these proteins can only interact through their respective FDH or CDH regions. Also consistent with the in vitro data, T7-FLAME-2 interacted with Mch4 and Mch5b (FIG. 3E). The yeast-two hybrid analysis confirmed the interactions of FLAME-1-FDH with FADD, Mch4 and Mch5 FDH regions (Table 1). Mch4-FDH (residues 18–189), Mch5b (FDH A, residues 3–80; FDH B, residues 102–177; FDH, residues 3–177), FLAME-1-FDH (residues 1–160), and murine FADD-DED (residues 1–78) were subcloned into yeast two-hybrid vectors. Yeast-two hybrid analysis was then performed. This analysis also revealed that FLAME-1-FDH can also strongly interact with itself (Table 1).

FADD can recruit Mch5 (MACH/FLICE) and possibly Mch4 to the Fas/TNFR1 signaling complex. To determine whether FLAME-1 can also be recruited through FADD, coprecipitation experiments were performed in 293T cells (FIG. 3F). FLAME-1 or FLAME-1-D341A were able to form a complex with Fas (lanes 4 and 8), possibly through interaction with endogenous FADD. Cotransfection of exogenous T7-FADD enhanced the FLAME-1-Fas interaction (lanes 5 and 7). The p39 fragment which is generated by cleavage at Asp341 also formed a complex with Fas (lane 5). These observations demonstrate that FLAME-1 can be recruited to a Fas signaling complex and, thus, may participate in the Fas signaling pathway. FLAME-2, on the other hand, did not form a complex with Fas in the presence or absence of exogenous FADD. However, it is still possible that FLAME-2 could interact with the Fas-death complex through other molecules that might be limited in the cell, such as Mch4 or Mch5.

Figure 4A:
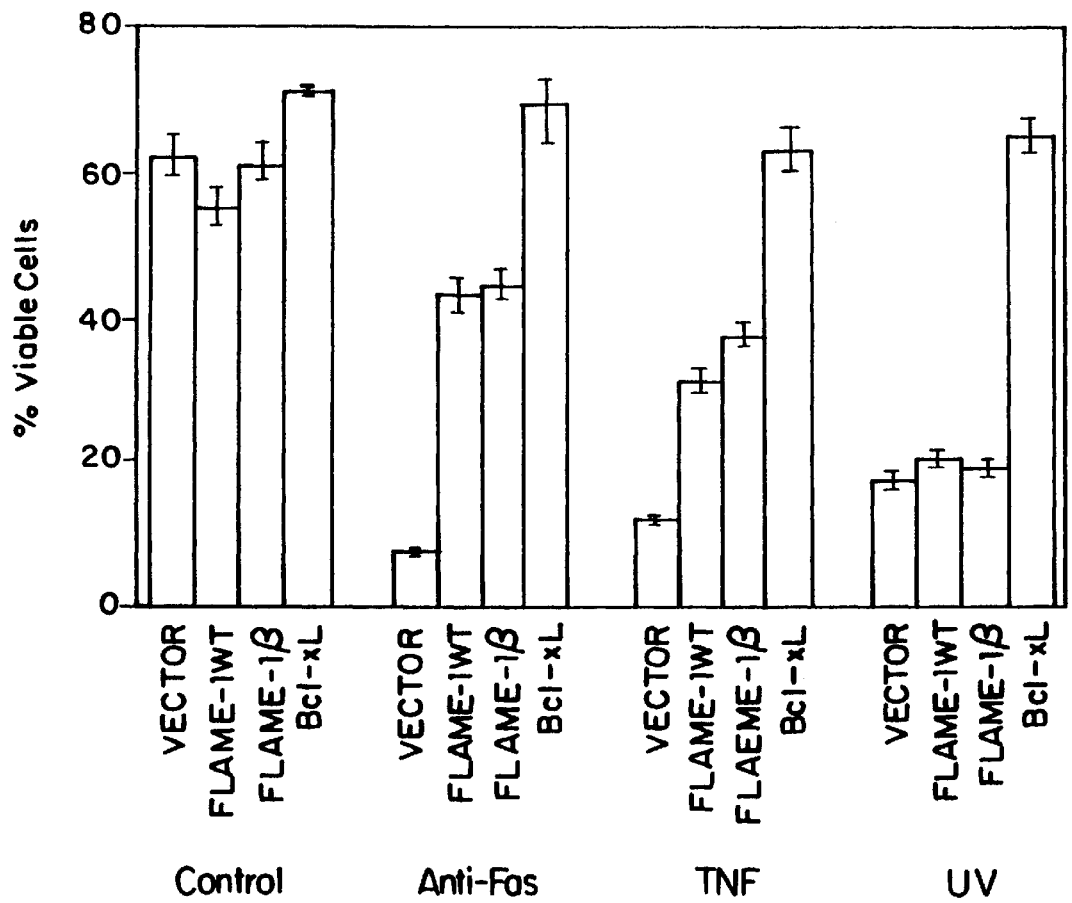
FIGS. 4A and 4B show FLAME-1 and FLAME-2 protect cells against apoptosis.
Figure 4B:
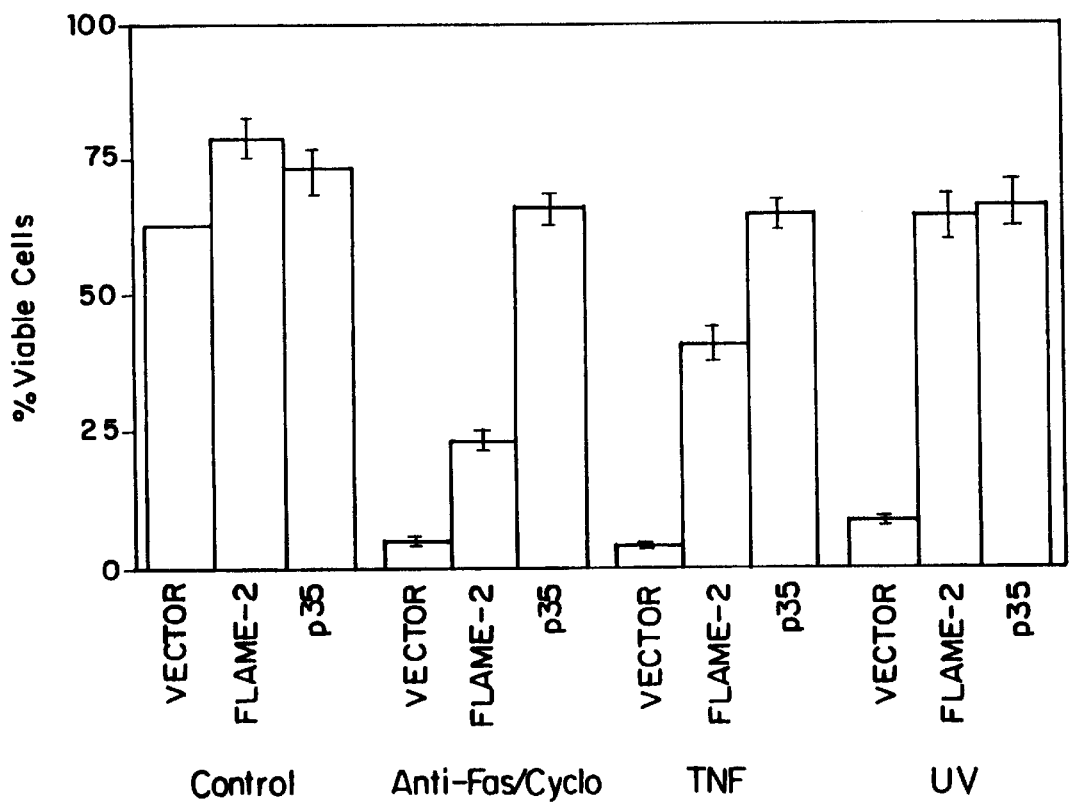

To study the functional role of FLAME-1 or 2 in Fas/TNFR1- or UV-induced apoptosis, they were transfected into MCF-7-FAS cells. FIGS. 4A and 4B show MCF7-FAS cells were transfected with the indicated expression plasmids. Cells were treated 28 h after transfection with either anti-Fas antibody, TNF, or UV-irradiation. MCF7-FAS cells were transiently cotransfected with reporter and test plasmids at a ratio of 1:10 and assayed for apoptosis. The percentage of viable cells (mean±SD) under each condition was determined by measuring the number of viable blue cells compared with total blue cells. Control cells received no treatment. The cells were fixed, stained for b-GAL expression and then viewed by phase-contrast microscopy. Neither FLAME-1 nor 2 induced apoptosis in these cells. However, FLAME-1 and FLAME-1b significantly blocked Fas- and TNFR1-induced apoptosis but not UV-induced apoptosis (FIG. 1A). This indicates that overexpression of the FDH regions of FLAME-1 is sufficient to block Fas/TNFR1-induced apoptosis. This protective effect approached 60–65% of that observed by Bcl-xL overexpression. FLAME-2, on the other hand, effectively blocked UV-induced apoptosis to a level approaching that observed by overexpression of baculovirus p35, and to a lesser degree inhibited TNFR1-induced apoptosis. Slight inhibition of Fas-induced apoptosis was also observed.

Taken together, the data presented here establish FLAME-1 and -2 as the first examples of endogenous FDH-containing proteins which can act as negative regulators of apoptosis. Recently, viral FDH-containing proteins E8 and MC159 were demonstrated to abrogate Fas/TNFR1 mediated apoptosis (Bertin, J. et al., 1997 Proc. Natl. Acad. Sci. USA. 94, 1172–1176). Both FLAME-1 and the viral proteins appear to target the Fas/FADD/caspase signaling complex by a potential dominant negative mechanism. Binding of FLAME-1, its FDH regions or the viral proteins to the caspase Mch4 or Mch5 or the adaptor molecule FADD blocks Fas/TNFR1-induced apoptosis possibly by interfering with the assembly of a functional death receptor signaling complex. In contrast to FLAME-1 and the viral proteins, FLAME-2 significantly abrogated UV-induced apoptosis. Recently, UV stimulation of cells was shown to lead to the activation of cell surface TNF receptors. Although FLAME-2 does significantly inhibit TNF mediated death, a purely TNF mediated UV-induced cell death is not supported here; This is because FLAME-1 possesses significant inhibitory activity towards TNF-induced death, yet it has no anti-apoptotic activity against UV. These results suggest that UV-induced apoptosis may be mediated by a novel FDH-containing adaptor molecule(s), which may be the target(s) for FLAME-2 anti-apoptotic activity. Consequently, it appears that molecules which contain FDH regions could be either pro-apoptotic like FADD, Mch4 or Mch5, or anti-apoptotic such as FLAME-1, FLAME-2 and the viral proteins E8 and MC159. Since the pro-apoptotic or anti-apoptotic proteins might have different expression levels, their ratios could determines how a given cell or cell type respond to FasL, TNF or UV. Targeted knockout of these molecules should help understand their exact role in apoptosis and other biological processes.

TABLE 1

FADD Domain Homology (FDH) interactions by the yeast two-hybrid assay.

| DNA-binding hybrid | Activation hybrid | Liquid assay b-gal activity, Miller units |
|---|---|---|
| LexA-FLAME-1-FDH | B42 | 23.2 ± 0.8 |
| LexA-FLAME-1-FDH | B42-Mch5b-FDH-A | 52.7 ± 22.6 |
| LexA-FLAME-1-FDH | B42-Mch5b-FDH-B | 728.1 ± 38.5 |
| LexA-FLAME-1-FDH | B42-Mch5b-FDH | 300.2 ± 42.3 |
| LexA-FLAME-1-FDH | B42-Mch4-FDH | 697.6 ± 103.6 |
| LexA-FLAME-1-FDH | B42-FADD-DED | 324.1 ± 34.0 |
| LexA-FLAME-1-FDH | B42-FLAME-1-FDH | 1634.0 ± 297.0 |

Data represent four independent experiments.

What is claimed is:

1. A substantially pure protein having the amino acid sequence of SEQ ID NO:4.

2. An isolated, substantially pure fragment of the FLAME-2 protein consisting of amino acid residues 1–106 of SEQ ID NO:4.

3. A substantially pure protein having the amino acid sequence of SEQ ID NO:4 or a fragment thereof comprising amino acid residues 1–106 of SEQ ID NO:4.

* * * * *

UNITED STATES PATENT AND TRADEMARK OFFICE
CERTIFICATE OF CORRECTION

PATENT NO. : 6,207,801 B1
DATED : March 27, 2001
INVENTOR(S) : Emad S. Alnemri

Page 1 of 1

It is certified that error appears in the above-identified patent and that said Letters Patent is hereby corrected as shown below:

Column 11,
Line 56, "referred" should be -- preferred -- and it should continue from the previous line starting with letter A.

Signed and Sealed this

Eighth Day of January, 2002

Attest:

JAMES E. ROGAN
*Attesting Officer*  *Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 1750 base pairs
       (B) TYPE: nucleic acid
       (C) STRANDEDNESS: double
       (D) TOPOLOGY: both (ii) MOLECULE TYPE: cDNA (ix) FEATURE:
       (A) NAME/KEY: CDS
       (B) LOCATION: 413..1750

(xi) SEQUENCE DESCRIPTION: SEQ ID NO:1:

```
CGAGTCTCAA CTAAAAGGGA CTCCCGGAGC TAGGGGTGGG GACTCGGCCT CACACAGTGA      60

GTGCCGGCTA TTGGACTTTT GTCCAGTGAC AGCTGAGACA ACAAGGACCA CGGGAGGAGG     120

TGTAGGAGAG AAGCGCCGCG AACAGCGATC GCCCAGCACC AAGTCCGCTT CCAGGCTTTC     180

GGTTTCTTTG CCTCCATCTT GGGTGCGCCT TCCCGGCGTC TAGGGGAGCG AAGGCTGAGG     240

TGGCAGCGGC AGGAGAGTCC GGCCGCGACA GGACGAACTC CCCCACTGGA AAGGATTCTG     300

AAAGAAATGA AGTCAGCCCT CAGAAATGAA GTTGACTGCC TGCTGGCTTT CTGTTGACTG     360

GCCCGGAGCT GTACTGCAAG ACCCTTGTGA GCTTCCCTAG TCTAAGAGTA GG ATG         415
                                                          Met
                                                           1

TCT GCT GAA GTC ATC CAT CAG GTT GAA GAA GCA CTT GAT ACA GAT GAG       463
Ser Ala Glu Val Ile His Gln Val Glu Glu Ala Leu Asp Thr Asp Glu
            5                  10                  15

AAG GAG ATG CTG CTC TTT TTG TGC CGG GAT GTT GCT ATA GAT GTG GTT       511
Lys Glu Met Leu Leu Phe Leu Cys Arg Asp Val Ala Ile Asp Val Val
        20                  25                  30

CCA CCT AAT GTC AGG GAC CTT CTG GAT ATT TTA CGG GAA AGA GGT AAG       559
Pro Pro Asn Val Arg Asp Leu Leu Asp Ile Leu Arg Glu Arg Gly Lys
    35                  40                  45

CTG TCT GTC GGG GAC TTG GCT GAA CTG CTC TAC AGA GTG AGG CGA TTT       607
Leu Ser Val Gly Asp Leu Ala Glu Leu Leu Tyr Arg Val Arg Arg Phe
 50                  55                  60                  65

GAC CTG CTC AAA CGT ATC TTG AAG ATG GAC AGA AAA GCT GTG GAG ACC       655
Asp Leu Leu Lys Arg Ile Leu Lys Met Asp Arg Lys Ala Val Glu Thr
                70                  75                  80

CAC CTG CTC AGG AAC CCT CAC CTT GTT TCG GAC TAT AGA GTG CTG ATG       703
His Leu Leu Arg Asn Pro His Leu Val Ser Asp Tyr Arg Val Leu Met
            85                  90                  95

GCA GAG ATT GGT GAG GAT TTG GAT AAA TCT GAT GTG TCC TCA TTA ATT       751
Ala Glu Ile Gly Glu Asp Leu Asp Lys Ser Asp Val Ser Ser Leu Ile
        100                 105                 110

TTC CTC ATG AAG GAT TAC ATG GGC CGA GGC AAG ATA AGC AAG GAG AAG       799
Phe Leu Met Lys Asp Tyr Met Gly Arg Gly Lys Ile Ser Lys Glu Lys
    115                 120                 125

AGT TTC TTG GAC CTT GTG GTT GAG TTG GAG AAA CTA AAT CTG GTT GCC       847
Ser Phe Leu Asp Leu Val Val Glu Leu Glu Lys Leu Asn Leu Val Ala
130                 135                 140                 145

CCA GAT CAA CTG GAT TTA TTA GAA AAA TGC CTA AAG AAC ATC CAC AGA       895
Pro Asp Gln Leu Asp Leu Leu Glu Lys Cys Leu Lys Asn Ile His Arg
                150                 155                 160
```

```
ATA GAC CTG AAG ACA AAA ATC CAG AAG TAC AAG CAG TCT GTT CAA GGA        943
Ile Asp Leu Lys Thr Lys Ile Gln Lys Tyr Lys Gln Ser Val Gln Gly
            165                 170                 175

GCA GGG ACA AGT TAC AGG AAT GTT CTC CAA GCA GCA ATC CAA AAG AGT        991
Ala Gly Thr Ser Tyr Arg Asn Val Leu Gln Ala Ala Ile Gln Lys Ser
            180                 185                 190

CTC AAG GAT CCT TCA AAT AAC TTC AGG AGC ATA CCT GAA GAG AGA TAC       1039
Leu Lys Asp Pro Ser Asn Asn Phe Arg Ser Ile Pro Glu Glu Arg Tyr
            195                 200                 205

AAG ATG AAG AGC AAG CCC CTA GGA ATC TGC CTG ATA ATC GAT TGC ATT       1087
Lys Met Lys Ser Lys Pro Leu Gly Ile Cys Leu Ile Ile Asp Cys Ile
210                 215                 220                 225

GGC AAT GAG ACA GAG CTT CTT CGA GAC ACC TTC ACT TCC CTG GGC TAT       1135
Gly Asn Glu Thr Glu Leu Leu Arg Asp Thr Phe Thr Ser Leu Gly Tyr
            230                 235                 240

GAA GTC CAG AAA TTC TTG CAT CTC AGT ATG CAT GGT ATA TCC CAG ATT       1183
Glu Val Gln Lys Phe Leu His Leu Ser Met His Gly Ile Ser Gln Ile
            245                 250                 255

CTT GGC CAA TTT GCC TGT ATG CCC GAG CAC CGA GAC TAC GAC AGC TTT       1231
Leu Gly Gln Phe Ala Cys Met Pro Glu His Arg Asp Tyr Asp Ser Phe
            260                 265                 270

GTG TGT GTC CTG GTG AGC CGA GGA GGC TCC CAG AGT GTG TAT GGT GTG       1279
Val Cys Val Leu Val Ser Arg Gly Gly Ser Gln Ser Val Tyr Gly Val
            275                 280                 285

GAT CAG ACT CAC TCA GGG CTC CCC CTG CAT CAC ATC AGG AGG ATG TTC       1327
Asp Gln Thr His Ser Gly Leu Pro Leu His His Ile Arg Arg Met Phe
290                 295                 300                 305

ATG GGA GAT TCA TGC CCT TAT CTA GCA GGG AAG CCA AAG ATG TTT TTT       1375
Met Gly Asp Ser Cys Pro Tyr Leu Ala Gly Lys Pro Lys Met Phe Phe
            310                 315                 320

ATT CAG AAC TAT GTG GTG TCA GAG GGC CAG CTG GAG GAC AGC AGC CTC       1423
Ile Gln Asn Tyr Val Val Ser Glu Gly Gln Leu Glu Asp Ser Ser Leu
            325                 330                 335

TTG GAG GTG GAT GGG CCA GCG ATG AAG AAT GTG GAA TTC AAG GCT CAG       1471
Leu Glu Val Asp Gly Pro Ala Met Lys Asn Val Glu Phe Lys Ala Gln
            340                 345                 350

AAG CGA GGG CTG TGC ACA GTT CAC CGA GAA GCT GAC TTC TTC TGG AGC       1519
Lys Arg Gly Leu Cys Thr Val His Arg Glu Ala Asp Phe Phe Trp Ser
355                 360                 365

CTG TGT ACT GCG GAC ATG TCC CTG CTG GAG CAG TCT CAC AGC TCA CCG       1567
Leu Cys Thr Ala Asp Met Ser Leu Leu Glu Gln Ser His Ser Ser Pro
370                 375                 380                 385

TCC CTG TAC CTG CAG TGC CTC TCC CAG AAA CTG AGA CAA GAA AGA AAA       1615
Ser Leu Tyr Leu Gln Cys Leu Ser Gln Lys Leu Arg Gln Glu Arg Lys
            390                 395                 400

CGC CCA CTC CTG GAT CTT CAC ATT GAA CTC AAT GGC TAC ATG TAT GAT       1663
Arg Pro Leu Leu Asp Leu His Ile Glu Leu Asn Gly Tyr Met Tyr Asp
            405                 410                 415

TGG AAC AGC AGA GTT TCT GCC AAG GAG AAA TAT TAT GTT TGG CTG CAG       1711
Trp Asn Ser Arg Val Ser Ala Lys Glu Lys Tyr Tyr Val Trp Leu Gln
            420                 425                 430

CAC ACT CTG AGA AAG AAA CTT ATC CTC TCC TAC ACA TAA                   1750
His Thr Leu Arg Lys Lys Leu Ile Leu Ser Tyr Thr *
    435                 440                 445

(2) INFORMATION FOR SEQ ID NO:2:

(i) SEQUENCE CHARACTERISTICS:
        (A) LENGTH: 445 amino acids
        (B) TYPE: amino acid
```

(D) TOPOLOGY: linear (ii) MOLECULE TYPE: protein (xi) SEQUENCE DESCRIPTION: SEQ ID NO:2:

Met Ser Ala Glu Val Ile His Gln Val Glu Glu Ala Leu Asp Thr Asp
 1               5                  10                  15

Glu Lys Glu Met Leu Leu Phe Leu Cys Arg Asp Val Ala Ile Asp Val
            20                  25                  30

Val Pro Pro Asn Val Arg Asp Leu Leu Asp Ile Leu Arg Glu Arg Gly
        35                  40                  45

Lys Leu Ser Val Gly Asp Leu Ala Glu Leu Leu Tyr Arg Val Arg Arg
    50                  55                  60

Phe Asp Leu Leu Lys Arg Ile Leu Lys Met Asp Arg Lys Ala Val Glu
 65                  70                  75                  80

Thr His Leu Leu Arg Asn Pro His Leu Val Ser Asp Tyr Arg Val Leu
                85                  90                  95

Met Ala Glu Ile Gly Glu Asp Leu Asp Lys Ser Asp Val Ser Ser Leu
            100                 105                 110

Ile Phe Leu Met Lys Asp Tyr Met Gly Arg Gly Lys Ile Ser Lys Glu
        115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Ser Ile Pro Glu Glu Arg
        195                 200                 205

Tyr Lys Met Lys Ser Lys Pro Leu Gly Ile Cys Leu Ile Ile Asp Cys
    210                 215                 220

Ile Gly Asn Glu Thr Glu Leu Leu Arg Asp Thr Phe Thr Ser Leu Gly
225                 230                 235                 240

Tyr Glu Val Gln Lys Phe Leu His Leu Ser Met His Gly Ile Ser Gln
                245                 250                 255

Ile Leu Gly Gln Phe Ala Cys Met Pro Glu His Arg Asp Tyr Asp Ser
            260                 265                 270

Phe Val Cys Val Leu Val Ser Arg Gly Gly Ser Gln Ser Val Tyr Gly
        275                 280                 285

Val Asp Gln Thr His Ser Gly Leu Pro Leu His His Ile Arg Arg Met
    290                 295                 300

Phe Met Gly Asp Ser Cys Pro Tyr Leu Ala Gly Lys Pro Lys Met Phe
305                 310                 315                 320

Phe Ile Gln Asn Tyr Val Val Ser Glu Gly Gln Leu Glu Asp Ser Ser
                325                 330                 335

Leu Leu Glu Val Asp Gly Pro Ala Met Lys Asn Val Glu Phe Lys Ala
            340                 345                 350

Gln Lys Arg Gly Leu Cys Thr Val His Arg Glu Ala Asp Phe Phe Trp
        355                 360                 365

Ser Leu Cys Thr Ala Asp Met Ser Leu Leu Glu Gln Ser His Ser Ser
    370                 375                 380

Pro Ser Leu Tyr Leu Gln Cys Leu Ser Gln Lys Leu Arg Gln Glu Arg

```
385                 390                 395                 400
Lys Arg Pro Leu Leu Asp Leu His Ile Glu Leu Asn Gly Tyr Met Tyr
            405                 410                 415

Asp Trp Asn Ser Arg Val Ser Ala Lys Glu Lys Tyr Tyr Val Trp Leu
            420                 425                 430

Gln His Thr Leu Arg Lys Lys Leu Ile Leu Ser Tyr Thr
            435                 440                 445
```

(2) INFORMATION FOR SEQ ID NO:3:

(i) SEQUENCE CHARACTERISTICS:
        (A) LENGTH: 1044 amino acids
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 88..1044

(xi) SEQUENCE DESCRIPTION: SEQ ID NO:3:

```
GGGAAATTAA GTTTCTTGCG GAGTACGGTG GGGATTGCAG CTGCTGAGCA GGGATTCTGG        60

AAAGCATTGC GTACCTGAGC CCCCAGC ATG GCG GGC CTA AAG CGG CGG GCA          111
                            Met Ala Gly Leu Lys Arg Arg Ala
                                                        450

AGC CAG GTG TGG CCA GAA GAG CAT GGT GAG CAG GAA CAT GGG CTG TAC        159
Ser Gln Val Trp Pro Glu Glu His Gly Glu Gln Glu His Gly Leu Tyr
455                 460                 465                 470

AGC CTG CAC CGC ATG TTT GAC ATC GTG GGC ACT CAT CTG ACA CAC AGA        207
Ser Leu His Arg Met Phe Asp Ile Val Gly Thr His Leu Thr His Arg
                475                 480                 485

GAT GTG CGC GTG CTT TCT TTC CTC TTT GTT GAT GTC ATT GAT GAC CAC        255
Asp Val Arg Val Leu Ser Phe Leu Phe Val Asp Val Ile Asp Asp His
            490                 495                 500

GAG CGT GGA CTC ATC CGA AAT GGA CGT GAC TTC TTA TTG GCA CTG GAG        303
Glu Arg Gly Leu Ile Arg Asn Gly Arg Asp Phe Leu Leu Ala Leu Glu
        505                 510                 515

CGC CAG GGC CGC TGT GAT GAA AGT AAC TTT CGC CAG GTG CTG CAG CTG        351
Arg Gln Gly Arg Cys Asp Glu Ser Asn Phe Arg Gln Val Leu Gln Leu
    520                 525                 530

CTG CGC ATC ATC ACT CGC CAC GAC CTG CTG CCC TAC GTC ACC CTC AAG        399
Leu Arg Ile Ile Thr Arg His Asp Leu Leu Pro Tyr Val Thr Leu Lys
535                 540                 545                 550

AGG AGA CGG GCT GTG TGC CCT GAT CTT GTA GAC AAG TAT CTG GAG GAG        447
Arg Arg Arg Ala Val Cys Pro Asp Leu Val Asp Lys Tyr Leu Glu Glu
                555                 560                 565

ACA TCA ATT CGC TAT GTG ACC CCC AGA GCC CTC AGT GAT CCA GAA CCA        495
Thr Ser Ile Arg Tyr Val Thr Pro Arg Ala Leu Ser Asp Pro Glu Pro
            570                 575                 580

AGG CCT CCC CAG CCC TCT AAA ACA GTG CCT CCC CAC TAT CCT GTG GTG        543
Arg Pro Pro Gln Pro Ser Lys Thr Val Pro Pro His Tyr Pro Val Val
        585                 590                 595

TGT TGC CCC ACT TCG GGT CCT CAG ATG TGT AGC AAG CGG CCA GCC CGA        591
Cys Cys Pro Thr Ser Gly Pro Gln Met Cys Ser Lys Arg Pro Ala Arg
    600                 605                 610

GGG AGA GCC ACA CTT GGG AGC CAG CGA AAA CGC CGG AAG TCA GTG ACA        639
Gly Arg Ala Thr Leu Gly Ser Gln Arg Lys Arg Arg Lys Ser Val Thr
615                 620                 625                 630

CCA GAT CCC AAG GAG AAG CAG ACA TGT GAC ATC AGA CTG CGG GTT CGG        687
```

-continued

```
Pro Asp Pro Lys Glu Lys Gln Thr Cys Asp Ile Arg Leu Arg Val Arg
                635                 640                 645

GCT GAA TAC TGC CAG CAT GAG ACT GCT CTG CAG GGC AAT GTC TTC TCT       735
Ala Glu Tyr Cys Gln His Glu Thr Ala Leu Gln Gly Asn Val Phe Ser
            650                 655                 660

AAC AAG CAG GAC CCA CTT GAG CGC CAG TTT GAG CGC TTT AAC CAG GCC       783
Asn Lys Gln Asp Pro Leu Glu Arg Gln Phe Glu Arg Phe Asn Gln Ala
                665                 670                 675

AAC ACC ATC CTC AAG TCC CGG GAC CTG GGC TCC ATC ATC TGT GAC ATC       831
Asn Thr Ile Leu Lys Ser Arg Asp Leu Gly Ser Ile Ile Cys Asp Ile
        680                 685                 690

AAG TTC TCT GAG CTC ACC TAC CTC GAT GCA TTC TGG CGT GAC TAC ATC       879
Lys Phe Ser Glu Leu Thr Tyr Leu Asp Ala Phe Trp Arg Asp Tyr Ile
695                 700                 705                 710

AAT GGC TCT TTA TTA GAG GCA CTT AAA GGT GTC TTC ATC ACA GAC TCC       927
Asn Gly Ser Leu Leu Glu Ala Leu Lys Gly Val Phe Ile Thr Asp Ser
                715                 720                 725

CTC AAG CAA GCT GTG GGC CAT GAA GCC ATC AAG CTG CTG GTA AAT GTA       975
Leu Lys Gln Ala Val Gly His Glu Ala Ile Lys Leu Leu Val Asn Val
            730                 735                 740

GAC GAG GAG GAC TAT GAG CTG GGC CGA CAG AAA CTC CTG AGG AAC TTG      1023
Asp Glu Glu Asp Tyr Glu Leu Gly Arg Gln Lys Leu Leu Arg Asn Leu
                745                 750                 755

ATG CTG CAA GCT TTG CCC TGA A                                        1045
Met Leu Gln Ala Leu Pro
760                 765
```

(2) INFORMATION FOR SEQ ID NO:4:

(i) SEQUENCE CHARACTERISTICS:
        (A) LENGTH: 318 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Gly Leu Lys Arg Arg Ala Ser Gln Val Trp Pro Glu Glu His
  1               5                  10                  15

Gly Glu Gln Glu His Gly Leu Tyr Ser Leu His Arg Met Phe Asp Ile
                 20                  25                  30

Val Gly Thr His Leu Thr His Arg Asp Val Arg Val Leu Ser Phe Leu
             35                  40                  45

Phe Val Asp Val Ile Asp Asp His Glu Arg Gly Leu Ile Arg Asn Gly
         50                  55                  60

Arg Asp Phe Leu Leu Ala Leu Glu Arg Gln Gly Arg Cys Asp Glu Ser
 65                  70                  75                  80

Asn Phe Arg Gln Val Leu Gln Leu Leu Arg Ile Ile Thr Arg His Asp
                 85                  90                  95

Leu Leu Pro Tyr Val Thr Leu Lys Arg Arg Ala Val Cys Pro Asp
                100                 105                 110

Leu Val Asp Lys Tyr Leu Glu Glu Thr Ser Ile Arg Tyr Val Thr Pro
            115                 120                 125

Arg Ala Leu Ser Asp Pro Glu Pro Arg Pro Gln Pro Ser Lys Thr
        130                 135                 140

Val Pro Pro His Tyr Pro Val Val Cys Pro Thr Ser Gly Pro Gln
145                 150                 155                 160

Met Cys Ser Lys Arg Pro Ala Arg Gly Arg Ala Thr Leu Gly Ser Gln
                165                 170                 175
```

```
Arg Lys Arg Arg Lys Ser Val Thr Pro Asp Pro Lys Glu Lys Gln Thr
            180                 185                 190

Cys Asp Ile Arg Leu Arg Val Arg Ala Glu Tyr Cys Gln His Glu Thr
            195                 200                 205

Ala Leu Gln Gly Asn Val Phe Ser Asn Lys Gln Asp Pro Leu Glu Arg
            210                 215                 220

Gln Phe Glu Arg Phe Asn Gln Ala Asn Thr Ile Leu Lys Ser Arg Asp
225                 230                 235                 240

Leu Gly Ser Ile Ile Cys Asp Ile Lys Phe Ser Glu Leu Thr Tyr Leu
                245                 250                 255

Asp Ala Phe Trp Arg Asp Tyr Ile Asn Gly Ser Leu Leu Glu Ala Leu
            260                 265                 270

Lys Gly Val Phe Ile Thr Asp Ser Leu Lys Gln Ala Val Gly His Glu
            275                 280                 285

Ala Ile Lys Leu Leu Val Asn Val Asp Glu Glu Asp Tyr Glu Leu Gly
            290                 295                 300

Arg Gln Lys Leu Leu Arg Asn Leu Met Leu Gln Ala Leu Pro
305                 310                 315

(2) INFORMATION FOR SEQ ID NO:5:

(i) SEQUENCE CHARACTERISTICS:
        (A) LENGTH: 1199 amino acids
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 32..988

(xi) SEQUENCE DESCRIPTION: SEQ ID NO:5:

CTGGAAAGCA CTCTATTTCT GAGCCTCTAG C ATG GCG GGC CTA AAG AGG CGG         52
                                 Met Ala Gly Leu Lys Arg Arg
                                     320             325

GCA AGC CAG GTG TGG CCC GAA GAG CGT GGG GAG CAA GAA CAT GGG CTC       100
Ala Ser Gln Val Trp Pro Glu Glu Arg Gly Glu Gln Glu His Gly Leu
            330                 335                 340

TAC AGC CTC CAC CGC ATG TTC GAC ATC GTG GGC ACC CAC CTA ACA CAC       148
Tyr Ser Leu His Arg Met Phe Asp Ile Val Gly Thr His Leu Thr His
            345                 350                 355

AGA GAT GTC CGA GTG CTT TCC TTC CTT TTT GTT GAT GTT ATT GAT GAC       196
Arg Asp Val Arg Val Leu Ser Phe Leu Phe Val Asp Val Ile Asp Asp
            360                 365                 370

CAT GAA CGT GGA CTC ATC CGA AAT GGA CGT GAC TTC TTA TTG GCA CTG       244
His Glu Arg Gly Leu Ile Arg Asn Gly Arg Asp Phe Leu Leu Ala Leu
375                 380                 385                 390

GAG CGC CAG GGC CGC TGT GAC GAG AGT AAC TTT CGC CAG GTG CTG CAG       292
Glu Arg Gln Gly Arg Cys Asp Glu Ser Asn Phe Arg Gln Val Leu Gln
            395                 400                 405

CTG CTG CGC ATC ATC ACT CGC CAT GAC TTG CTG CCC TAC GTT ACT CTC       340
Leu Leu Arg Ile Ile Thr Arg His Asp Leu Leu Pro Tyr Val Thr Leu
            410                 415                 420

AAG AAG AGA CGA GCT GTG TGC CCT GAT CTT GTA GAC AAG TAT CTG GAG       388
Lys Lys Arg Arg Ala Val Cys Pro Asp Leu Val Asp Lys Tyr Leu Glu
            425                 430                 435

GAA ACA TCA ATT CGC TAT GTG ACC CCC AGA GCC CTC AGT GAC CCA GAA       436
Glu Thr Ser Ile Arg Tyr Val Thr Pro Arg Ala Leu Ser Asp Pro Glu
```

```
                440             445             450
CCG AGG CCT CCC CAG CCC TCT AAA ACA GTG CCT CCC CAC TAT CCT GTG         484
Pro Arg Pro Pro Gln Pro Ser Lys Thr Val Pro Pro His Tyr Pro Val
455             460             465             470

GTG TGC TGC CCC ACT TCG GGT TCT CAA ATG TGT AGT AAG CGG CCA GCC         532
Val Cys Cys Pro Thr Ser Gly Ser Gln Met Cys Ser Lys Arg Pro Ala
                475             480             485

CGA GGG AGA ACC ACA CTT GGG AGC CAG CGA AAA CGC GGG AAG TCG GTG         580
Arg Gly Arg Thr Thr Leu Gly Ser Gln Arg Lys Arg Arg Lys Ser Val
                490             495             500

ACA CCA GAC CCG AAG GAA AAG CAG ACA TGT GAT ATC AGG CTC CGA GTT         628
Thr Pro Asp Pro Lys Glu Lys Gln Thr Cys Asp Ile Arg Leu Arg Val
        505             510             515

CGG GCG GAA TAC TGC CAG CAT GAG ACG GCT CTG CAA GGC AAT GTC TTC         676
Arg Ala Glu Tyr Cys Gln His Glu Thr Ala Leu Gln Gly Asn Val Phe
        520             525             530

TCC AAT AAG CAG GAC CCA CTT GAG CGC CAG TTT GAG CGC TTT AAC CAG         724
Ser Asn Lys Gln Asp Pro Leu Glu Arg Gln Phe Glu Arg Phe Asn Gln
535             540             545             550

GCC AAC ACT ATC CTC AAG TCC CGG GAC CTG GGC TCC ATC ATC TGT GAC         772
Ala Asn Thr Ile Leu Lys Ser Arg Asp Leu Gly Ser Ile Ile Cys Asp
                555             560             565

ATC AAG TTC TCT GAG CTC ACC TAC CTC GAC GCA TTC TGG CGA GAC TAC         820
Ile Lys Phe Ser Glu Leu Thr Tyr Leu Asp Ala Phe Trp Arg Asp Tyr
                570             575             580

ATT AAT GGC TCA TTA TTA GAG GCA CTG AAA GGT GTC TTC ATC ACA GAC         868
Ile Asn Gly Ser Leu Leu Glu Ala Leu Lys Gly Val Phe Ile Thr Asp
                585             590             595

TCT CTC AAG CAA GCT GTG GGC CAT GAA GCC ATC AAG CTG CTG GTG AAC         916
Ser Leu Lys Gln Ala Val Gly His Glu Ala Ile Lys Leu Leu Val Asn
        600             605             610

GTG GAT GAG GAG GAC TAT GAG CTG GGC CGA CAG AAA CTC CTG AGG AAC         964
Val Asp Glu Glu Asp Tyr Glu Leu Gly Arg Gln Lys Leu Leu Arg Asn
615             620             625             630

TTG ATG CTG CAG GCA TTA CCC TGA CCTTTCCCCT TCTCACCTTT CTGGGGACTG      1018
Leu Met Leu Gln Ala Leu Pro
                635

TTCGCTCCGT CACCTCTGGA GCTGACATAC TGTTCTGGGG TTTGTTCTCT ACCCTTTCCA     1078

ACCAATCACA CCGCCTTTTT TTTTTTTTTT TTTTAAAAGG AAAAGACAAA GGAAGGTGGA     1138

AGTGGTGTCC CTGCCCTCCC TGCACCCATG TGCCTGGGCT TCCCCGTTTC CTGTTGCCAC     1198

TT                                                                    1200

(2) INFORMATION FOR SEQ ID NO:6:

(i) SEQUENCE CHARACTERISTICS:
        (A) LENGTH:  318 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Gly Leu Lys Arg Arg Ala Ser Gln Val Trp Pro Glu Arg
 1               5                  10                  15

Gly Glu Gln Glu His Gly Leu Tyr Ser Leu His Arg Met Phe Asp Ile
                20                  25                  30

Val Gly Thr His Leu Thr His Arg Asp Val Arg Val Leu Ser Phe Leu
            35                  40                  45
```

```
Phe Val Asp Val Ile Asp Asp His Glu Arg Gly Leu Ile Arg Asn Gly
            50                  55                  60

Arg Asp Phe Leu Leu Ala Leu Glu Arg Gln Gly Arg Cys Asp Glu Ser
 65              70                  75                      80

Asn Phe Arg Gln Val Leu Gln Leu Leu Arg Ile Ile Thr Arg His Asp
                 85                  90                  95

Leu Leu Pro Tyr Val Thr Leu Lys Lys Arg Arg Ala Val Cys Pro Asp
            100                 105                 110

Leu Val Asp Lys Tyr Leu Glu Glu Thr Ser Ile Arg Tyr Val Thr Pro
            115                 120                 125

Arg Ala Leu Ser Asp Pro Glu Pro Arg Pro Pro Gln Pro Ser Lys Thr
 130                 135                 140

Val Pro Pro His Tyr Pro Val Val Cys Cys Pro Thr Ser Gly Ser Gln
 145                 150                 155                 160

Met Cys Ser Lys Arg Pro Ala Arg Gly Arg Thr Thr Leu Gly Ser Gln
                 165                 170                 175

Arg Lys Arg Arg Lys Ser Val Thr Pro Asp Pro Lys Glu Lys Gln Thr
                 180                 185                 190

Cys Asp Ile Arg Leu Arg Val Arg Ala Glu Tyr Cys Gln His Glu Thr
                 195                 200                 205

Ala Leu Gln Gly Asn Val Phe Ser Asn Lys Gln Asp Pro Leu Glu Arg
 210                 215                 220

Gln Phe Glu Arg Phe Asn Gln Ala Asn Thr Ile Leu Lys Ser Arg Asp
225                 230                 235                 240

Leu Gly Ser Ile Ile Cys Asp Ile Lys Phe Ser Glu Leu Thr Tyr Leu
                 245                 250                 255

Asp Ala Phe Trp Arg Asp Tyr Ile Asn Gly Ser Leu Leu Glu Ala Leu
                 260                 265                 270

Lys Gly Val Phe Ile Thr Asp Ser Leu Lys Gln Ala Val Gly His Glu
                 275                 280                 285

Ala Ile Lys Leu Leu Val Asn Val Asp Glu Glu Asp Tyr Glu Leu Gly
 290                 295                 300

Arg Gln Lys Leu Leu Arg Asn Leu Met Leu Gln Ala Leu Pro
305                 310                 315

(2) INFORMATION FOR SEQ ID NO:7:

(i) SEQUENCE CHARACTERISTICS:
        (A) LENGTH: 17 amino acids
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

AGGCTGGTCT CGAACTCC                                                18

(2) INFORMATION FOR SEQ ID NO:8:

(i) SEQUENCE CHARACTERISTICS:
        (A) LENGTH: 17 amino acids
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:
```

```
TTCTCCAAGC AGCAATCC                                                         18
```

(2) INFORMATION FOR SEQ ID NO:9:

(i) SEQUENCE CHARACTERISTICS:
        (A) LENGTH: 17 amino acids
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GGCCTCCCAA AGTGCTGG                                                         18
```

(2) INFORMATION FOR SEQ ID NO:10:

(i) SEQUENCE CHARACTERISTICS:
        (A) LENGTH: 17 amino acids
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TTCAGGCTCC ATAATGGG                                                         18
```

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:11:

Gln Ala Cys Gln Gly
           5

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:12:

Gln Asn Tyr Val Val
           5

(2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:13:

Gln Ala Cys Arg Gly (2) INFORMATION FOR SEQ ID NO:14:

```
    (i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:14:

Gln Ala Cys Gly Gly (2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:15:

Leu Glu Val Asp Gly (2) INFORMATION FOR SEQ ID NO:16:

(i) SEQUENCE CHARACTERISTICS:
        (A) LENGTH: 7 amino acids
        (B) TYPE: amino acid
        (D) TOPOLOGY: unknown (ii) MOLECULE TYPE: protein (xi) SEQUENCE DESCRIPTION: SEQ ID NO:16:

Tyr Val Ala Asp Ala Met Cys (2) INFORMATION FOR SEQ ID NO:17:

(i) SEQUENCE CHARACTERISTICS:
        (A) LENGTH: 7 amino acids
        (B) TYPE: amino acid
        (D) TOPOLOGY: unknown (ii) MOLECULE TYPE: protein (xi) SEQUENCE DESCRIPTION: SEQ ID NO:17:

Asp Glu Val Asp Ala Met Cys
```